United States Patent [19]

Blackburn et al.

[11] 4,435,405
[45] Mar. 6, 1984

[54] QUINOLINE DERIVATIVES WHICH ARE 5-HYDROXYTRYPTAMINE ANTAGONISTS

[75] Inventors: Thomas P. Blackburn, Congleton; Barry Cox, Chorltonville; Allen J. Guildford, Sandbach; David J. Le Count, Congleton; Robert J. Pearce, Wilmslow; Craig W. Thornber, MacClesfield, all of England

[73] Assignee: Imperial Chemical Industries PLC, London, England

[21] Appl. No.: 382,116

[22] Filed: May 26, 1982

[30] Foreign Application Priority Data

Jun. 9, 1981 [GB] United Kingdom ............... 8117642

[51] Int. Cl.$^3$ .................. A61K 31/47; C07D 215/36
[52] U.S. Cl. ................... 424/258; 546/157; 546/167; 546/173; 546/180
[58] Field of Search ................... 546/157; 424/258

[56] References Cited

U.S. PATENT DOCUMENTS

| Re. 16,394 | 7/1926 | Callsen ........................ 546/157 |
| 1,572,768 | 2/1926 | Callsen ........................ 546/157 |
| 1,860,286 | 5/1932 | Hartmann et al. .......... 546/157 X |
| 4,343,805 | 8/1982 | Crossley et al. .............. 424/263 |

FOREIGN PATENT DOCUMENTS

| 430960 | 6/1926 | Fed. Rep. of Germany ...... 546/157 |
| 1049379 | 1/1959 | Fed. Rep. of Germany ...... 424/267 |

OTHER PUBLICATIONS

Zayed et al., Chemical Abstracts, vol. 89, 215199v (1978).

Gilman et al., J. Am. Chem. Soc., vol. 71, pp. 3667–3668 (1949).
Westland et al., J. Med. Chem., vol. 16(4), pp. 328–331 (1973).
Zayed et al., Pharmazie, 33, No. 9, pp. 572–575 (1978).

Primary Examiner—Donald G. Daus
Assistant Examiner—Diana G. Rivers
Attorney, Agent, or Firm—Cushman, Darby & Cushman

[57] ABSTRACT

Compounds of the formula:

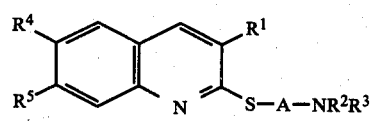

wherein A stands for the radical —$(CH_2)_2$— which may bear one or two defined substituents; $R^1$ stands for a (3-4C) alkyl or cyclopropyl radical, or a phenyl radical which may optionally bear one or two defined substituents, or a heteroaryl radical of five or six ring atoms which may optionally bear a (1-3C)alkyl substituent; $R^2$ and $R^3$ stand for hydrogen or a (1-2C)alkyl radical, or $R^2$ stands for a (2-4C)alkylene radical which is linked to one of the carbon atoms forming the two-carbon-atom-backbone of A so as to form, together with the adjacent nitrogen atom, a pyrrolidinyl or piperidyl radical; and one of $R^4$ and $R^5$ stands for hydrogen, and the other stands for hydrogen, a halogen atom or a (1-3C)alkyl or (1-3C)alkoxy radical; and acid-addition salts thereof. Processes for the manufacture of said compounds. Pharmaceutical compositions comprising one of said compounds and a pharmaceutical diluent or carrier. The compounds are 5-hydroxytryptamine antagonists.

7 Claims, No Drawings

QUINOLINE DERIVATIVES WHICH ARE 5-HYDROXYTRYPTAMINE ANTAGONISTS

This invention relates to quinoline derivatives which are active as 5-hydroxytryptamine antagonists in warmblooded animals.

The compounds of the invention are quinoline derivatives which are characterised by the presence of a substituted aminoalkylthio substituent, or the like, at position 2 and a defined substituent, for example a phenyl radical, at position 3. Compounds of this type are novel, but chemically related compounds have been described in the literature. Thus, 3-aryl-4-aminoalkylthioquinoline derivatives, for example 4-(3-dimethylaminopropylthio)-3-phenylquinoline, which are position isomers of some of the compounds of the invention, are described in German patent specification No. 1,049,379. These known compounds are stated to exhibit nicotinolytic and anti-inflammatory activity, and to exhibit inhibitory activity on parasympathetic ganglia. Position isomers of lower homologues of some of the compounds of the invention, for example 2-(2-diethylaminoethylthio)-4-methylquinoline, are described in J.Amer.Chem.Soc. 1949, 71, 3667. Finally, 2-(2-diethylaminoethoxy)-3-phenylquinoline, which has an oxygen/sulphur relationship to one of the compounds of the invention, is described in U.S. patent specification No. 1,860,286, and it is stated therein to exhibit antipyretic activity.

According to the invention there are provided quinoline derivatives of the formula:

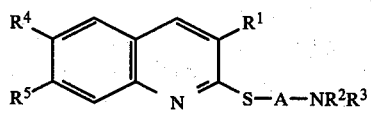

wherein:

A stands for the radical —(CH$_2$)$_2$—, which may optionally be substituted by one or two (1-2C) alkyl radicals or it may be substituted by an alkylene radical so as to form, together with the residue of the —(CH$_2$)$_2$— radical, a cycloalkylene radical of not more than 6 carbon atoms;

R$^1$ stands for an n-, iso- or s-(3-4C)alkyl radical, or a cyclopropyl radical, or R$^1$ stands for a phenyl radical which may optionally be substituted with one or two substituents, in the latter case the same or different substituents, selected from halogen atoms and hydroxy, (1-4C)alkyl, (1-4C)alkoxy, (1-4C)alkylthio, (1-2C)perfluoroalkyl, cyano, carboxy, (1-2C)alkoxy-carbonyl, carbamoyl, N-[(1-3C)alkyl]-carbamoyl and N,N-di-[(1-3C)alkyl]carbamoyl radicals, or R$^1$ stands for a heteroaryl radical of five or six ring atoms containing a single hetero-atom selected from oxygen, sulfur and nitrogen atoms or containing two hetero-atoms which are either a nitrogen atom and a sulphur atom or a nitrogen atom and an oxygen atom, which heteroaryl radical may optionally be substituted with a (1-3C)alkyl radical;

R$^2$ and R$^3$, wich may be the same or different, stand for hydrogen or a methyl or ethyl radical, or R$^2$ stands for a dimethylene, trimethylene or tetramethylene radical which is linked to one or other of the carbon atoms forming the two-carbon-atom-backbone of the radical A so as to form, together with the adjacent nitrogen atom, a pyrrolidinyl or piperidyl radical; and one of R$^4$ and R$^5$ stands for hydrogen, and the other stands for hydrogen, a halogen atom, or a (1-3C)alkyl or (1-3C)alkoxy radical;

and pharmaceutically-acceptable acid-addition salts thereof.

Some of the compounds of the invention possess at least one asymmetric carbon atom; for example this is the case when A stands for a 1,2-propylene radical. The racemic form of such compounds possessing at least one asymmetric carbon atom can be resolved by conventional methods into the optically active isomers thereof. It is to be understood that the compounds of this invention consist of (a) the compounds of formula I in racemic form, and (b) the optical isomers thereof which are 5-hydroxytryptamine (5-HT) antagonists.

A may, for example, stand for a 1,2-ethylene, 1,2-propylene, 2,3-propylene, 1,1-dimethyl-1,2-ethylene, 2,2-dimethyl-1,2-ethylene, cyclopropylene, 1,2-cis-cyclohexylene or 1,2-trans-cyclohexylene radical.

R$^1$ may, for example, stand for an n-propyl, isopropyl, n-butyl, s-butyl or cyclopropyl radical. Alternatively, R$^1$ may, for example, stand for a phenyl radical which may optionally be substituted by one or two substituents, in the latter case the same or different substituents, selected from fluorine, chlorine and bromine atoms, and hydroxy, (1-2C)alkyl, for example methyl, (1-4C)alkoxy, for example methoxy or n-propoxy, (1-2C)alkylthio, for example methylthio, trifluoromethyl, cyano, carboxy, (1-2C)alkoxy-carbonyl, for example methoxycarbonyl, carbamoyl, N-[(1-2C)alkyl]carbamoyl, for example N-methylcarbamoyl, and N,N-di-[(1-2C)alkyl]-carbamoyl, for example N,N-dimethylcarbamoyl, radicals. Alternatively, R$^1$ may, for example, stand for a furyl, thienyl, pyridyl, thiazolyl or oxazolyl radical, which may optionally be substituted by a (1-2C)alkyl radical, for example a methyl radical.

One of R$^4$ and R$^5$ stands for hydrogen, and the other may, for example, stand for hydrogen, a fluorine, chlorine or bromine atom, a (1-2C)alkyl radical, for example a methyl radical, or a (1-4C)alkoxy radical, for example a methoxy or n-propoxy radical.

According to one embodiment of the invention there are provided quinoline derivatives of the formula I wherein:

A stands for the radical —(CH$_2$)$_2$—, which may optionally be substituted by one or two methyl radicals, or it may be substituted by an alkylene radical so as to form, together with the residue of the —(CH$_2$)$_2$— radical, a cycloalkylene radical of not more than 6 carbon atoms;

R$^1$ stands for an n-propyl, isopropyl, n-butyl or cyclopropyl radical, or it stands for a phenyl radical which may optionally be substituted with one or two substituents, in the latter case the same or different substituents, selected from halogen atoms and hydroxy, methyl, methoxy, n-propoxy, methylthio, trifluoromethyl, cyano, carboxy, methoxycarbonyl, carbamoyl, N-methylcarbamoyl and N,N-dimethylcarbamoyl radicals, or R$^1$ stands for a heteroaryl radical of five or six ring atoms containing a single hetero-atom selected from oxygen, sulphur and nitrogen atoms or containing two hetero-atoms which are either a nitrogen atom and a sulphur atom or a nitrogen atom and an oxygen atom, which heteroaryl radical may optionally be substituted with a methyl radical;

$R^2$ and $R^3$, which may be the same or different, stand for hydrogen or a methyl radical, or $R^2$ stands for a dimethylene, trimethylene or tetramethylene radical which is linked to one or other of the carbon atoms forming the two-carbon-atom-backbone of A so as to form, together with the adjacent nitrogen atom, a piperidyl radical; one of $R^4$ and $R^5$ stands for hydrogen, and the other of $R^4$ and $R^5$ stands for hydrogen, a halogen atom, or a methyl or methoxy radical;

and pharmaceutically-acceptable acid-addition salts thereof.

A group of preferred compounds of the invention consists of 2-(2-dimethylaminoethylthio)-3-isopropylquinoline, 2-(2-dimethylaminoethylthio)-3-p-fluorophenylquinoline, 2-(2-dimethylaminoethylthio)-3-o-methoxyphenylquinoline, 2-(2-dimethylaminoethylthio)-3-p-tolylquinoline, 2-(2-dimethylamino-2-methylpropylthio)-3-phenylquinoline and 2-(2-dimethylaminopropylthio)-3-phenylquinoline, and pharmaceutically-acceptable acid-addition salts thereof. Particularly preferred compounds of the invention are 2-(2-dimethylaminoethylthio)-3-phenylquinoline and pharmaceutically-acceptable acid-addition salts thereof.

Suitable salts of the invention are derived from inorganic or organic acids which provide a pharmaceutically-acceptable anion, for example hydrochloric, phosphoric, citric, tartaric, succinic or benzoic acid, and acids, for example 2-hydroxy-3-naphthoic or 1,1'-methylene-bis-2-hydroxy-3-naphthoic acid, which afford salts which are relatively insoluble in water and therefore have long-acting characteristics.

The compounds of the invention, and the compounds used as starting materials in the processes of the invention, may be obtained by processes which are known for the preparation of chemically analogous compounds. A compound containing at least one asymmetric carbon atom which is used as a starting material in a process of the invention may be used in racemic or optically active form.

According to a further feature of the invention there is provided a process for the manufacture of the compounds of the formula I, wherein A, $R^1$, $R^2$, $R^3$, $R^4$ and $R^5$ have the meanings stated above, and pharmaceutically-acceptable acid-addition salts thereof, which comprises reacting a compound of the formula:

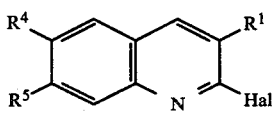
II wherein Hal stands for a halogen atom and $R^1$, $R^4$ and $R^5$ have the meanings stated above, with a compound of the formula:

 III wherein A, $R^2$ and $R^3$ have the meanings stated above, or an acid-addition salt thereof, in the presence of an acid-binding agent.

Hal may, for example, stand for a chlorine or bromine atom. The salt of the compound of the formula III may, for example, be a salt derived from an inorganic acid, for example a hydrohalic acid, for example hydrochloric acid. The acid-binding agent may, for example, be sodium hydride. The reaction is conveniently carried out in a suitable organic solvent, for example dimethylformamide, and it may be accelerated or completed by the application of heat.

According to a further feature of the invention there is provided a process for the manufacture of the compounds of the formula I, wherein A, $R^1$, $R^2$, $R^3$, $R^4$ and $R^5$ have the meanings stated above, and pharmaceutically-acceptable acid-addition salts thereof, which comprises reacting a compound of the formula:

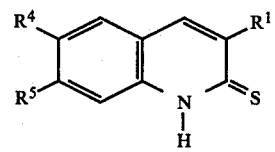
IV wherein $R^1$, $R^4$ and $R^5$ have the meanings stated above, with a compound of the formula:

 V wherein Z stands for a halogen atom or an arenesulphonyloxy or alkanesulphonyloxy radical, and A, $R^2$ and $R^3$ have the meanings stated above, or an acid-addition salt thereof, in the presence of an acid-binding agent.

Z may, for example, stand for a chlorine or bromine atom or a p-toluenesulphonyloxy or methanesulphonyloxy radical. The salt of the compound of the formula V may, for example, be a salt derived from an inorganic acid, for example a hydrohalic acid, for example hydrochloric acid. The acid-binding agent may, for example, be sodium hydride. The reaction is conveniently carried out in a suitable organic solvent, for example dimethylformamide, and it may be carried out at ambient temperature or at a moderately elevated temperature.

According to a further feature of the invention there is provided a process for the manufacture of compounds of the formula:

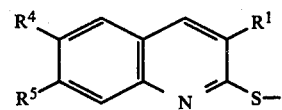
VI wherein $R^1$, $R^3$, $R^4$ and $R^5$ have the meanings stated above, X stands for a methylene radical, optionally substituted by one or two (1-2C)alkyl radicals and $R^6$ stands for a (1-2C)alkyl radical, and pharmaceutically-acceptable acid-addition salts thereof, which comprises reacting a compound of the formula:

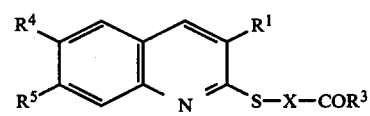
VII with an amine of the formula $R^3R^6NH$ under reducing conditions, and wherein $R^1$, $R^3$, $R^4$, $R^5$, $R^6$ and X have the meanings stated above.

The reducing conditions may be provided by the use of (a) a borohydride derivative having reducing properties, for example sodium cyanoborohydride, or (b) hydrogen in the presence of a hydrogenation catalyst, for example palladium-on-charcoal. Both types of reaction are preferably carried out at ambient temperature. Process (a) is conveniently carried out in a suitable organic solvent, for example, a (1-3C)alkanol, for example ethanol, optionally together with acetic acid. Process (b) is conveniently carried out in a suitable organic solvent, for example a (1-3C)alkanol, for example ethanol. It is to be understood that where any part of the compound of the formula VII is susceptible to reduction or hydrogenolysis if catalytic hydrogenation is employed, then process (a) should be used (with, for example, sodium borohydride as the reducing agent) to avoid such unwanted side-reactions.

According to a further feature of the invention there is provided a process for the manufacture of compounds of the formula:

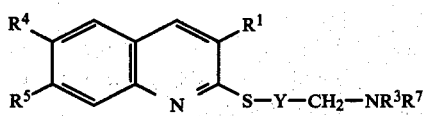

VIII and pharmaceutically-acceptable acid-addition salts thereof, which comprises reducing an amide of the formula:

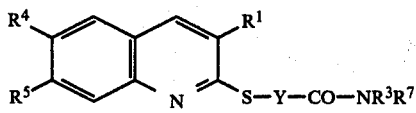

IX wherein $R^1$, $R^3$, $R^4$ and $R^5$ have the meanings stated above, provided that $R^1$ cannot stand for a phenyl radical bearing a cyano, carbamoyl, N-[(1-3C)alkyl]-carbamoyl or N,N-di-[(1-3C)alkyl]carbamoyl substituent, $R^7$ stands for hydrogen or a (1-2C)alkyl radical, and Y stands for a methylene radical optionally substituted with one or two (1-2C)alkyl radicals, or $R^7$ stands for a dimethylene, trimethylene or tetramethylene radical which is linked to Y so as to form, together with the adjacent nitrogen atom, a pyrrolidinyl or piperidyl radical.

A suitable reducing agent is, for example, a borane complex having reducing properties, for example a borane-dimethyl sulphide complex, or an aluminium hydride derivative having reducing properties, for example lithium aluminium hydride or sodium bis-(2-methoxyethoxy)aluminium hydride ('Red-al' is the Trade Mark for a 3.4 M-solution in toluene). In the case where $R^1$ stands for a phenyl radical bearing a carboxy substituent, said borane-complex is not a suitable reducing agent and consequently said aluminium hydride derivative should be used. Conversely, in the case where $R^1$ stands for a phenyl radical bearing a (1-2C)-alkoxy-carbonyl substituent, said aluminium hydride derivative is not a suitable reducing agent and therefore said borane complex should be used. The reduction is carried out in a suitable organic solvent, for example tetrahydrofuran, and it may be accelerated or completed by the application of heat.

According to a further feature of the invention there is provided a process for the manufacture of compounds of the formula:

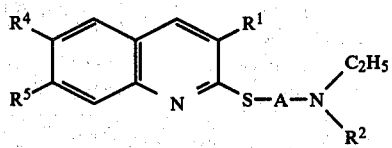

X and pharmaceutically-acceptable acid-addition salts thereof, which comprises reducing a compound of the formula:

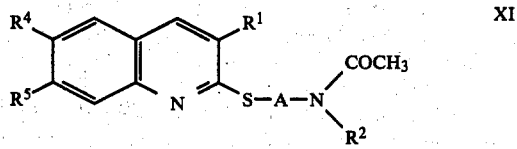

XI and wherein A, $R^1$, $R^2$, $R^4$ and $R^5$ have the meanings stated above, provided that $R^1$ cannot stand for a phenyl radical bearing a cyano, carbamoyl, N-[(1-3C)-alkyl]-carbamoyl or N,N-di-[(1-3C)alkyl]carbamoyl substituent.

A suitable reducing agent is, for example, a borane complex having reducing properties, for example a borane-dimethyl sulphide complex, or an aluminium hydride derivative having reducing properties, for example lithium aluminium hydride or sodium bis-(2-methoxyethoxy)aluminium hydride. In the case where $R^1$ stands for a phenyl radical bearing a carboxy substituent, said borane complex is not a suitable reducing agent and consequently said aluminium hydride derivative should be used. Conversely, in the case where $R^1$ stands for a phenyl radical bearng a (1-2C)alkoxy-carbonyl substituent, said aluminium hydride derivative is not a suitable reducing agent and therefore said borane complex should be used. The reduction is carried out in a suitable organic solvent, for example tetrahydrofuran. It is preferably carried out in an inert atmosphere, for example under argon, and it may be accelerated or completed by the application of heat.

According to a further feature of the invention there is provided a process for the manufacture of compounds of the formula:

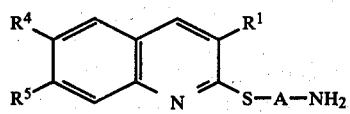

XII and pharmaceutically-acceptable acid-addition salts thereof, which comprises carrying out a Curtius reaction on a compound of the formula:

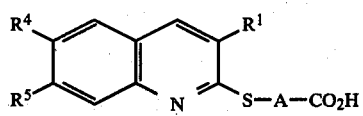

XIII and wherein A, $R^1$, $R^4$ and $R^5$ have the meanings stated above, provided that $R^1$ cannot stand for a carboxyphenyl radical.

The Curtius reaction is well known in the chemical art, and in essence it consists in converting a carboxylic acid successively into the corresponding azide, the corresponding transient isocyanate, a corresponding urethane derivative, and finally into the desired amine. In the present case the azide may, for example, be obtained by reacting the carboxylic acid (XIII) with diphenylphosphoryl azide in the presence of a suitable solvent, for example toluene, and in an inert atmosphere, for example under argon, and the reaction may be accelerated or completed by the application of heat. The resulting azide may, for example, by converted into the corresponding urethane derivative by reacting it with 2-(trimethylsilyl)ethanol in a suitable solvent, for example toluene, in an inert atmosphere, for example under argon, and the reaction may be accelerated or completed by the application of heat. The final stage may, for example, be carried out by reacting the said urethane derivative with a source of fluoride ions, for example tetra-n-butylammonium fluoride, in a suitable organic solvent, for example a mixture of acetonitrile and tetrahydrofuran. The said final stage may be carried out in an inert atmosphere, for example under argon, and it may be accelerated or completed by the application of heat.

According to a further feature of the invention, therefore, there is provided a process for the manufacture of compounds of the formula XII, and pharmaceutically-acceptable acid-addition salts thereof, which comprises reacting a compound of the formula:

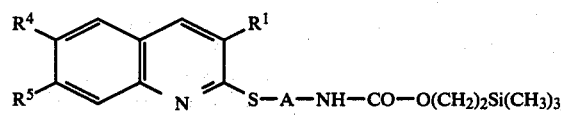

XIV with a source of fluoride ions, and wherein A, $R^1$, $R^4$ and $R^5$ have the meanings stated above.

The last-named process may be carried out as described immediately above.

According to a further feature of the invention there is provided a process for the manufacture of compounds of the formula:

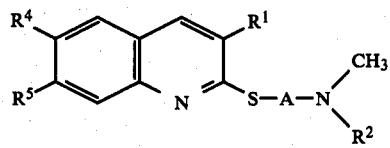

XV and pharmaceutically-acceptable acid-addition salts thereof, which comprises reducing a compound of the formula:

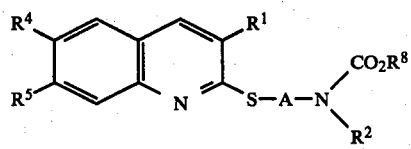

XVI and wherein A, $R^1$, $R^2$, $R^4$ and $R^5$ have the meanings stated above, provided that $R^1$ cannot stand for a phenyl radical bearing a cyano, (1-2C)alkoxy-carbonyl, carbamoyl, N-[(1-3C)alkyl]carbamoyl or N,N-di-[(1-3C)alkyl]carbamoyl substituent, and $R^8$ stands for a (1-5C)alkyl radical.

$R^8$ may, for example, stand for an ethyl radical. A suitable reducing agent is, for example, an aluminium hydride derivative having reducing properties, for example lithium aluminium hydride or sodium bis-(2-methoxyethoxy)aluminium hydride. The reduction may be carried out in a suitable organic solvent, for example di-(2-methoxyethyl)ether, in an inert atmosphere, for example under argon, and it may be accelerated or completed by the application of heat.

According to a further feature of the invention there is provided a process for the manufacture of those of the compounds of the invention which contain the group:

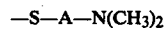

XVII or

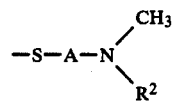

XVIII and pharmaceutically-acceptable acid-addition salts thereof, which comprises reacting the corresponding compound containing the group:

XIX or

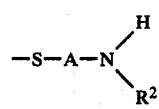

XX with formaldehyde and formic acid, and wherein A and $R^2$ have the meanings stated above.

The process may be accelerated or completed by the application of heat.

According to a further feature of the invention there is provided a process for the manufacture of compounds of the formula XII, and pharmaceutically-acceptable acid-addition salts thereof, which comprises reacting a compound of the formula:

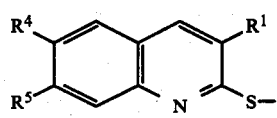

XXI with an alkali metal hydroxide under essentially anhydrous conditions, and wherein A, $R^1$, $R^4$, $R^5$ and $R^8$ have the meanings stated above, provided that $R^1$ cannot stand for a phenyl radical bearing a cyano, carboxy, (1-2C)alkoxy-carbonyl, carbamoyl, N-[(1-3C)-alkyl]carbamoyl or N,N-di-[(1-3C)alkyl]carbamoyl substituent.

The alkali metal hydroxide may, for example, be sodium hydroxide which is generated in situ from a sodium hydride-dimethylsulphoxide complex and the equivalent amount of water. The process may be carried out in a suitable organic solvent, for example dimethylsulphoxide, either at ambient temperature or at a moderately elevated temperature.

According to a further feature of the invention there is provided a process for the manufacture of compounds of the formula:

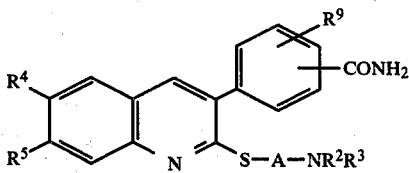

XXII and pharmaceutically-acceptable acid-addition salts thereof, which comprises hydrolysing a compound of the formula:

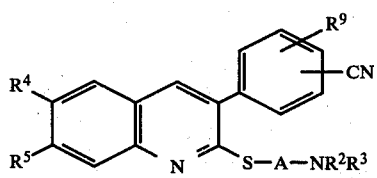

XXIII under alkaline conditions, wherein A, $R^2$, $R^3$, $R^4$ and $R^5$ have the meanings stated above, and $R^9$ stands for hydrogen, a halogen atom or a hydroxy, (1-4C)alkyl, (1-4C)alkoxy, (1-4C)alkylthio or (1-2C)perfluoroalkyl radical.

A suitable hydrolytic agent is, for example, an alkali metal hydroxide, for example potassium hydroxide. The hydrolysis is carried out in a suitable organic solvent, for example a (1-4C)alkanol, for example t-butanol, and it may be accelerated or completed by the application of heat.

According to a further feature of the invention there is provided a process for the manufacture of compounds of the formula:

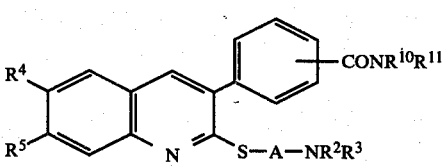

XXIV and pharmaceutically-acceptable acid-addition salts thereof, which comprises reacting a compound of the formula:

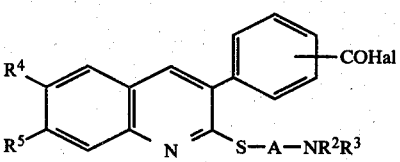

XXV with a compound of the formula $R^{10}R^{11}NH$, wherein $R^{10}$ and $R^{11}$, which may be the same or different, stand for hydrogen or a (1-3C)alkyl radical, and wherein A, $R^2$, $R^3$, $R^4$, $R^5$ and Hal have the meanings stated above.

A suitable value for Hal is, for example, a chlorine atom. The process may be carried out in a suitable organic solvent, for example toluene or methylene dichloride, or in an aqueous medium, and it may be accelerated or completed by the application of heat. When the compound of the formula $R^{10}R^{11}NH$ is dimethylamine it may be generated in situ by the use of dimethylformamide; in this case dimethylformamide may also be used as the solvent in which to carry out the reaction. The starting material of the formula XXV, wherein Hal stands for a chlorine atom, may, for example, be obtained by reacting the corresponding carboxylic acid with oxalyl chloride, together with a catalytic amount of dimethylformamide, in a suitable organic solvent, for example methylene dichloride, at ambient temperature.

According to a further feature of the invention there is provided a process for the manufacture of compounds of the formula:

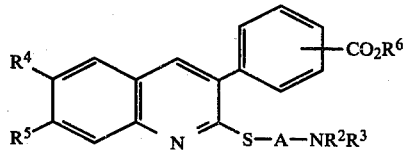

XXVI and pharmaceutically-acceptable acid-addition salts thereof, which comprises esterifying a compound of the formula:

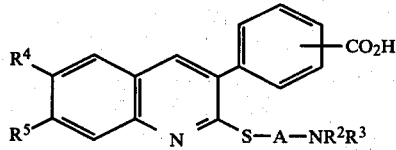

XXVII with methanol or ethanol, and wherein A, $R^2$, $R^3$, $R^4$, $R^5$ and $R^6$ have the meanings stated above.

The esterification may, for example, be carried out by reacting the carboxylic acid (XXVII) with a suitable acid halide, for example thionyl chloride, and reacting the resulting halide with methanol or ethanol. The process may be carried out at ambient temperature or at an elevated temperature.

According to a further feature of the invention there is provided a process for the manufacture of compounds of the formula:

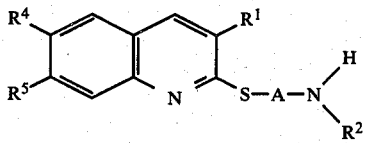

XXVIII and pharmaceutically-acceptable acid-addition salts thereof, which comprises reacting a compound of the formula:

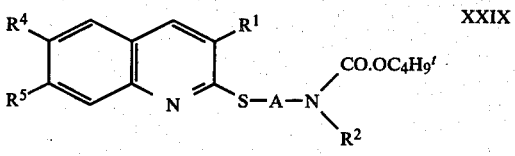

XXIX with an acid, and wherein A, $R^1$, $R^2$, $R^4$ and $R^5$ have the meanings above, provided that A cannot stand for a cyclopropylene radical.

A suitable acid is, for example, a hydrohalic acid, for example hydrogen chloride, or trifluoroacetic acid. Hydrogen chloride may be used in the form of an aqueous solution, for example at a concentration between 1 M and that of a saturated solution, or as a solution in an organic solvent, for example ethyl acetate, for example in the range 2 M to 6 M. When trifluoroacetic acid is used it may be used by itself or it may be diluted with 5-10% by volume of water. The process is conveniently carried out at ambient temperature.

According to a further feature of the invention there is provided a process for the manufacture of compounds of the formula:

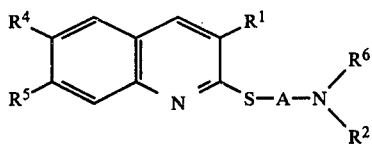

XXX and pharmaceutically-acceptable acid-addition salts thereof, which comprises reacting a compound of the formula XXVIII with a compound of the formula $R^6Hal$ and an acid-binding agent, and wherein A, $R^1$, $R^2$, $R^4$, $R^5$, $R^6$ and Hal have the meanings stated above provided that $R^1$ cannot stand for a phenyl radical bearing a hydroxy or carboxy substituent.

Hal may, for example, stand for an iodine atom. A suitable acid-binding agent is, for example, an alkali metal carbonate, for example potassium carbonate. The process is conveniently carried out in a suitable organic solvent, for example a (1-3C)alkanol, for example ethanol, and it may be carried out at ambient temperature or at an elevated temperature. It is to be understood that this process enables one to achieve monoalkylation, for example in the case where $R^2$ in the starting material stands for a methyl or ethyl radical, or dialkylation, for example where $R^2$ in the starting material stands for hydrogen.

According to a further feature of the invention there is provided a process for the manufacture of optically active compounds of the formula I and pharmaceutically-acceptable acid-addition salts thereof, which comprises resolving a compound of the formula I which contains at least one asymmetric carbon atom, and wherein $R^1$, $R^2$, $R^3$, $R^4$, $R^5$ and A have the meanings stated above.

A suitable resolving acid is, for example, an optical isomer of tartaric acid, dibenzoyltartaric acid, or di-(p-toluoyl)tartaric acid. The resolution is carried out in a suitable solvent, for example a (1-3C)alkanol, for example methanol or ethanol, optionally in admixture with water, ethyl acetate or diethyl ether.

The activity of the compounds of the invention as 5-HT antagonists has been demonstrated in the following tests:

(1) In vitro 5-HT receptor binding (a) Binding of tritiated 5-hydroxytryptamine ([$^3$H]5-HT)

This is an in vitro test of the affinity of test compounds for the central 5-HT$_1$ receptor (Molecular Pharmacology, 1979, 16, 687). The compounds are tested for their ability to displace [$^3$H]5-HT from a receptor site on a synaptosomal preparation prepared from rat brain tissue. The compounds are tested at 3 μg/ml., and they are declared active if they produce more than 30% inhibition of specific binding. Compounds of interest are tested at a range of concentrations to establish the absolute potency for this receptor. The results are expressed as PI$_{50}$ values, the PI$_{50}$ being the $-\log_{10}$ of the concentration of the compound needed to displace 50% of the specifically bound [$^3$H]5-HT.

(b) Binding of tritiated spiroperidol ([$^3$H]spiroperidol)

This is an in vitro test of the affinity of test compounds for the central 5-HT$_2$ receptor (Molecular Pharmacology, 1979, 16, 687). The compounds are tested for their ability to displace [$^3$H]spiroperidol from a receptor on a synaptosomal preparation prepared from rat brain cortex. The compounds are tested at 0.3 μg./ml., and they are declared active if they produce more than 30% inhibition of specific binding. Compounds of interest are tested at a range of concentrations as outlined above in respect of [$^3$H]5-HT binding. The results are expressed as PI$_{50}$ values, the PI$_{50}$ being the $-\log_{10}$ of the concentration of the compound needed to displace 50% of the specifically bound [$^3$H]spiroperidol (2) Inhibition of head twitches induced in mice by 5-hyroxytryptophan (5-HTP)

This is an in vivo test of activity at central 5-HT receptors. The test involves administering a precursor of 5-HT, i.e. 5-HTP, to mice. The resultant high levels of 5-HT produced in the brain are believed to be responsible for the spontaneous twitching of the head and ears seen for a period after the administration of 5-HTP. All known centrally acting 5-HT antagonists inhibit the twitching response in a dose-dependent manner.

A range of doses of the compounds under test are administered intraperitoneally to male mice (average weight 18-20 g.; in groups of 5) 15 minutes before an intraperitoneal injection of 5-HTP at 300 mg./kg. The mice are then observed 15 minutes later for head twitches, and the results are expressed as ID$_{50}$ values. Nonspecific inhibition of the response due, for example, to sedation is eliminated by determining the presence or absence of the pinna reflex to tactile stimulation of the ear.

(3) Antagonism of fenfluramine-induced hyperthermia in rats

This is a sensitive in vivo test which is based on the ability of fenfluramine to release 5-HT from endogenous neuronal stores.

Female rats (Alderley Park Strain; 180-220 g.) are housed (5 per cage) in a relatively warm environment (25°-28° C.) one hour prior to the beginning of the test to allow the animals to acclimatise. When the acclimatisation period is over, the rectal temperature of each animal is measured and these temperatures serve as the control reading from which all changes are calculated. For the recording of the control temperatures (-1 hour), either a test compound or the vehicle (distilled water) is administered orally or subcutaneously and after a further hour (0 hour) the rectal temperature of each rat is measured. A dose of 15 mg./kg. of fenfluramine, or distilled water (controls), is then injected intraperitoneally. Rectal temperatures are then measured at the following times after the administration of the fenfluramine or distilled water:

30 minutes, and 1,2,3,4,5 and 6 hours

The potency of a compound in the test is expressed as an ID$_{50}$ value, i.e. the dose of the compound which reduces the hyperthermic response to a standard dose of fenfluoramine by 50%.

The potency of a specific compound of the present invention depends upon its precise chemical structure, but generally speaking the compounds of the invention exhibit the following potencies in the following ranges in the above tests:

Test (1) (a): [$^3$H]5-HT binding: pI$_{50}$ 5–9,
Test (1) (b): [$^3$H]spiroperidol binding: pI$_{50}$ 5–9,
Test (2): ID$_{50}$ 0.1 to 50 mg./kg.
Test (3): ID$_{50}$ 0.1 to 50 mg./kg.

No toxic effects or other undesirable effects have been observed with the compounds at doses at which they are active in the abovementioned tests.

Illustrative LD$_{50}$ data for some compounds of the invention is as follows:

2-(2-dimethylaminoethylthio)-3-phenylquinoline hydrochloride

| Species | Sex | Route of administration | LD$_{50}$ (mg./kg.) |
| --- | --- | --- | --- |
| rat | female | oral | >1000 |
| rat | female | intraperitoneal | 128 |
| mouse | male | oral | 485 |
| mouse | male | intraperitoneal | 75 |

2-(2-dimethylaminoethylthio)-3-isopropylquinoline hydrochloride

LD$_{50}$ approx. 100 mg./kg. intraperitoneally in the mouse.

2-(2-dimethylaminoethylthio)-3-(o-methoxyphenyl)-quinoline hydrochloride

LD$_{50}$ approx. 150 mg./kg. intraperitoneally in the mouse.

Because of their activity as 5-HT antagonists the compounds of the invention may be used clinically in human patients as psychotropic agents for the treatment of diseases or dysfunctions of the central nervous system, for example psychoses, schizophrenia, mania, anxiety or depression, for the treatment of migraine, urticaria, asthma, hypertension, pulmonary hypertension, vascular spasm and gastrointestinal disorders, and for the inhibition of the aggregation of blood platelets. When one of the said compounds is used clinically in human patients it is recommended that it be dosed:

(a) orally at a dose of 0.5 mg./kg. to 100 mg./kg. at suitable intervals, for example three times per day, or (b) intramuscularly at a dose of 0.1 mg./kg. to 20 mg./kg. at suitable intervals, (c) by means of a depot injection (2.5 to 100 mg./kg.), or (d) rectally at a dose of 0.5 mg./kg. to 200 mg./kg.

According to a further feature of the invention there are provided pharmaceutical compositions comprising a compound of the formula I wherein A, R$^1$, R$^2$, R$^3$, R$^4$ and R$^5$ have the meanings stated above, or a pharmaceutically-acceptable acid-addition salt thereof, and an inert pharmaceutically-acceptable diluent or carrier.

The pharmaceutical compositions of the invention may be in a form suitable for oral, parenteral or rectal administration. Thus, for example, they may be in orally-administrable unit dosage form, for example tablets or capsules, which may optionally be adapted for sustained release, or in injectable form, for example a sterile injectable solution or suspension, or in the form of a suppository for rectal administration. The said pharmaceutical compositions may be produced by conventional methods using conventional diluents and carriers.

The pharmaceutical compositions of the invention may contain, in addition to a compound of the formula I, wherein A, R$^1$, R$^2$, R$^3$, R$^4$ and R$^5$ have the meanings stated above, or a pharmaceutically-acceptable acid-addition salt thereof, one or more of the following medicaments:

1. known psychotropic agents, for example antipsychotic agents, for example chlorpromazine, haloperidol or fluphenazine, or antidepressants, for example imipramine, mianserine or desmethylamitryptaline;
2. known anti-migraine agents, for example ergot alkaloids and derivatives thereof, and propranolol, clonidine, pitzotifen, O-acetylsalicylic acid or paracetamol;
3. known antihypertensive agents, for example α-methyldopa, α-adrenergic blocking agents, for example prazosin, β-adrenergic blocking agents, for example propranolol or atenolol, diuretics, for example hydrochlorothiazide or frusemide, and vasodilators, for example minoxidil or hydrallazine; and
4. known platelet aggregation inhibitors, for example dipyridamol, anturan, sulphinpyrazone, ticlopidine and O-acetylsalicyclic acid.

The invention is illustrated but not limited by the following Examples in which the temperatures are expressed in degrees Celsius, the evaporations were carried out under reduced pressure (approx. 15 mm.Hg) unless otherwise stated, and the petroleum ether used had b.p. 60°–80°:

EXAMPLE 1

2-Dimethylaminoethanethiol hydrochloride (3.4 g.) was added to a suspension of sodium hydride (2.32 g. of a 50% w/w dispersion in mineral oil) in dimethylformamide (25 ml.) at 0° to 5°. When all the hydrogen had evolved, 2-chloro-3-isopropylquinoline (4.0 g.) was added and the mixture heated at 80° for 5 hr. The reaction mixture was then poured into ice water (500 ml.) and extracted with ethyl acetate (3×120 ml.). The ethyl acetate extract was washed successively with water (100 ml.) and saturated brine (100 ml.) and then dried (MgSO$_4$). The ethyl acetate solution was evaporated and the residual oil was chromatographed on basic alumina (70 g.; Brockmann Grade III), eluted with increasing concentrations of chloroform in petroleum ether. The eluate obtained with 20% v/v chloroform in petroleum ether was evaporated, the residual oil was dissolved in diethyl ether, and ethereal hydrogen chloride was added until precipitation was complete. The solid residue was collected by filtration and crystallised from ethanol-diethyl ether to give 2-(2-dimethylaminoethylthio)-3-isopropylquinoline hydrochloride, m.p. 164°–7°.

The 2-chloro-3-isopropylquinoline used as starting material was obtained as follows:

Dimethylformamide (15.2 ml.) was added dropwise with stirring to phosphorus oxychloride (85 ml.) at 0°–5°. The mixture was stirred for 30 min. at 0°–5° and isovalerylanilide (15 g.) was then added. The mixture was heated at 75° for 16 hours, cooled, poured into ice-water (3 l.), and extracted with ethyl acetate (4×250 ml.). The ethyl acetate extract was washed successively with water (200 ml.) and saturated brine (200 ml.) and then dried (MgSO$_4$). The ethyl acetate solution was evaporated and the residal oil was chromatographed on silica (500 g. of Merck type 7739), eluted with increasing concentrations of chloroform in petroleum ether. The eluate obtained with 30% v/v chloroform in petroleum ether was evaporated to give 2-chloro-3-isopropylquinoline as a viscous oil which was used without further purification.

EXAMPLES 2–5

EXAMPLE 2

2-Dimethylaminoethanethiol hydrochloride (58.40 g. of 80% w/w) was added to a suspension of sodium hydride (31.68 g. of a 50% w/w dispersion in mineral oil) in dimethylformamide (500 ml.) at 0° to 5°. When all the hydrogen had evolved, a solution of 2-chloro-3-phenylquinoline (72.70 g.) in dimethylformamide (100 ml.) was added and the mixture stirred and heated at 75° for 5 hr. The reaction mixture was then poured into ice water (4000 ml.) and extracted with ethyl acetate (6×500 ml.). The ethyl acetate extract was washed succesively with water (1000 ml.) and saturated brine (1000 ml.), and then dried (MgSO4). The ethyl acetate solution was evaporated and the residual oil was chromatographed on basic alumina (1200 g.; Brockmann Grade III), eluted with increasing concentrations of chloroform in petroleum ether. The elutate obtained with 10% v/v chloroform in petroleum ether was evaporated. The residual solid was dissolved in ethanol (800 ml.) and treated with concentrated hydrochloric acid (25.2 ml.). The ethanol was evaporated, and the oily residue was azeotroped with toluene. The solid obtained was recrystallised from ethanol-diethyl ether and was then washed with a small volume of cold acetone. The mixture was filtered and there was obtained as the solid residue 2-(2-dimethylaminoethylthio)-3-phenyl-quinoline hydrochloride, m.p. 195°–8° C.

The above procedure was repeated using the appropriate 2-chloro-3-(substituted-phenyl)quinoline derivative as starting material and there were thus obtained the following compounds:

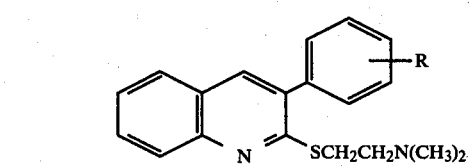

| Example Number | R | Salt | m.p. |
|---|---|---|---|
| 3 | p-F | HCl.½ H2O | 198–201 |
| 4 | p-CH3 | HCl | 165–6 |
| 5 | o-OCH3 | HCl | 214–6 |

The 2-chloro-3-(substituted-phenyl)quinoline derivatives used as starting materials were obtained as follows:

Preparation of anilides

A mixture of o-methoxyphenylacetic acid (10 g.), oxalyl chloride (10 ml.) and dimethylformamide (2 drops) was stirred at ambient temperature for 16 hr. The excess oxalyl chloride was evaporated, and the residue was dissolved in methylene dichloride (20 ml.) and added dropwise with stirring to an ice-cold solution of aniline (5.6 g.) and triethylamine (6.1 g.) in methylene dichloride (50 ml.). The mixture was stirred at ambient temperature for 16 hr., and then washed successively with 2 M-hydrochloric acid (25 ml.) and water (2×25 ml.), and dried (MgSO4). The methylene dichloride was evaporated and the residue was crystallised from ethyl acetate-petroleum ether to give o-methoxyphenylacetanilide, m.p. 204°–6°.

In a similar manner there were obtained:
p-fluorophenylacetanilide, m.p. 128°–131° (crystallised from toluene)
p-tolylacetanilide, m.p. 144°–7° (crystallised from toluene).

Preparation of chloroquinoline derivatives

The following compounds were prepared using the appropriate anilide derivative as starting material in an analogous manner to that described in Example 1 for the preparation of 2-chloro-3-isopropylquinoline:

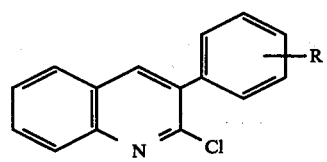

| R | m.p. |
|---|---|
| p-F | 88–90 |
| p-CH3 | oil |
| o-OCH3 | 84–5 |

EXAMPLE 6

Sodium hydride (1.92 g. of a 50% w/w dispersion in mineral oil) was added to a solution of 3-phenylquinolin-2-thione (4.74 g.) in dimethylformamide (50 ml.) at ambient temperature. When all the hydrogen had evolved, 2-methylaminoethyl chloride (2.6 g.) was added and the mixture was stirred at ambient temperature for 20 hours. The reaction mixture was then poured into water (600 ml.) and extracted with ethyl acetate (2×100 ml.). The ethyl acetate extract was washed with water (2×50 ml.) and then dried (MgSO4). The solvent was evaporated, and the residue was dissolved in diethyl ether (75 ml.) and treated with ethereal hydrogen chloride until precipitation was complete. The mixture was filtered and the solid residue was crystallised from ethanol-diethyl ether to give 2-(2-methylaminoethylthio)-3-phenylquinoline hydrochloride hemi-hydrate, m.p. 168°–170°.

The thione used as starting material was obtained as follows:

A mixture of 2-chloro-3-phenylquinoline (3.4 g.) and thiourea (1.2 g.) in ethanol (20 ml.) was refluxed for one hour. The solution was allowed to cool to ambient temperature and diethyl ether (10 ml.) was added. The solid which precipitated was filtered off, dispersed in M-sodium hydroxide (70 ml.), and heated on a steam bath for 2 hr. The reaction mixture was acidified with 2 M-hydrochloric acid. The resulting mixture was filtered, and the solid residue was stirred with hot ethanol (50 ml.) and filtered. There was thus obtained as the solid residue 3-phenylquinolin-2-thione, m.p. 242°–4°.

EXAMPLE 7

A solution of 2-(2-oxopropylthio)-3-phenylquinoline (2.2 g.) in dry ethanol (50 ml.) was added to a mixture of dimethylamine in ethanol (1 ml. of a 33% w/v solution) and glacial acetic acid (0.7 g.). Sodium cyanoborohydride (0.3 g.) was then added. The mixture was stirred for 18 hr. at ambient temperature in the presence of a molecular sieve (0.5 g. of Type 3A). More dimethylamine solution in ethanol (1.3 ml. of a 33% w/v solution), glacial acetic acid (0.9 g.) and sodium cyanoborohydride (0.3 g.) were then added and the mixture was stirred for 24 hr. at ambient temperature. The molecular sieve was filtered off, and the solution evaporated. 2 M-hydrochloric acid solution (20 ml.) was added to the residue and the mixture was washed with ethyl acetate (20 ml.). The aqueous phase was basified with 2 M-sodium hydroxide solution (25 ml.) and extracted with diethyl ether (3×50 ml.). The diethyl ether extract was washed with water (50 ml.) and dried (MgSO4). The diethyl ether solution was evaporated and the residue chromatographed on basic alumina (75 g. Brockmann Grade III), eluted with increasing concentrations of chloroform in petroleum ether. The eluate obtained with 20% v/v chloroform in petroleum ether was evaporated. The residue was dissolved in diethyl ether (20 ml.), and ethereal hydrogen chloride was added until precipitation was complete. The solid was collected by filtration and crystallised from ethanol-diethyl ether to give 2-(2-dimethylaminopropylthio)-3-phenylquinoline hydrochloride, m.p. 158°–160°.

The quinoline derivative used as starting material was obtained as follows:

3-Phenylquinolin-2-thione (3.5 g.) was added in portions to a stirred suspension of sodium hydride (0.72 g. of a 50% w/w dispersion in mineral oil) in dimethylformamide (50 ml.) at ambient temperatue. When all of the hydrogen had evolved, chloroacetone (1.5 g.) was added and the reaction mixture was stirred at ambient temperature for 18 hr. The reaction mixture was poured into water (400 ml.) and extracted with ethyl acetate (2×100 ml.). The ethyl acetate extract was washed with water (2×50 ml.) and dried (MgSO4). The solvent was evaporated and the residue was chromatographed on basic alumina (100 g., Brockmann Grade III), eluted with increasing concentrations of chloroform in petroleum ether. The eluate obtained with 10% v/v chloroform in petroleum ether was evaporated to give 2-(2-oxopropylthio)-3-phenylquinoline, m.p. 88°–90°.

EXAMPLE 8

Borane-dimethyl sulphide complex (10 to 10.2 M; 1.5 ml.) was added dropwise to a solution of 2-[1-(dimethylcarbamoyl)ethylthio]-3-phenylquinoline (2 g.) in dry tetrahydrofuran (50 ml.) at ambient temperature. The mixture was then heated gently under reflux for 6 hr. Methanol (20 ml.) was added, the mixture was stirred for 18 hr. at ambient temperature, and then refluxed for 2 hr. The solvent was evaporated and an excess of a saturated solution of hydrogen chloride in diethyl ether was added to the oily residue. The solvent was evaporated, and the residual oil dissolved in water (20 ml.), basified with 2 M-sodium hydroxide solution (10 ml.) and extracted with ethyl acetate (3×20 ml.). The ethyl acetate extract was washed with water (20 ml.) and then dried (MgSO4). The solvent was evaporated and the residual oil was chromatographed on basic alumina (20 g. of Brockmann Grade III), eluted with increasing concentrations of chloroform in petroleum ether. The eluate obtained with 50% v/v chloroform in petroleum ether was evaporated. The residual oil was dissolved in diethyl ether (20 ml.), and ethereal hydrogen chloride was added until precipitation was complete. The solid residue was collected by filtration and crystallised from ethanoldiethyl ether to give 2-[1-(dimethylaminomethyl)ethylthio]-3-phenylquinoline hydrochloride, m.p. 197°–200°.

The quinoline derivative used as starting material was obtained as follows:

3-Phenylquinolin-2-thione (4.74 g.; see Example 6) was added in portions to a well-stirred suspension of sodium hydride (1.06 g. of a 50% w/w dispersion in mineral oil) in dimethylformamide (25 ml.) at 0°–5°. After all the hydrogen gas had evolved, 2-chloro-N,N-dimethylacetamide (2.19 g.) was added and the mixture was heated at 80°. for 2 hr. The reaction mixture was then poured into water (300 ml.) and extracted with ethyl acetate (4×50 ml.). The ethyl acetate extract was washed with water (50 ml.) and then dried (MgSO4). The solvent was evaporated and the residual oil was chromatographed on basic alumina (70 g. of Brockmann Grade III), eluted with increasing concentrations of chloroform in petroleum ether. The eluate obtained with 20% v/v chloroform in petroleum ether was evaporated. The residual solid was crystallised from ethyl acetate-petroleum ether to give 2-(dimethylcarbamoylmethylthio)-3-phenylquinoline, m.p. 86°–9°.

To a solution of lithium di-isopropylamide [prepared from di-isopropylamine (6.2 ml.) and n-butyllithium (24.7 ml. of a 1.7 M solution in hexane) in dry tetrahydrofuran (100 ml.) at −78°. under argon] was added a solution of 2-(dimethylcarbamoylmethylthio)-3-phenylquinoline (6.6 g.) in dry tetrahydrofuran (50 ml.) at −60°. The mixture was then stirred for 15 min. at −60°. Iodomethane (2.7 ml.) was added and the mixture was allowed to warm up to ambient temperature. Glacial acetic acid (2.6 ml.) was then added, followed by water (200 ml.). The tetrahydrofuran phase was separated and retained, and the aqueous layer was extracted with ethyl acetate (2×30 ml.). The ethyl acetate and tetrahydrofuran phases were combined and dried (MgSO4). The solvent was evaporated and the residual oil was chromatographed on basic alumina (100 g. of Brockmann grade III) eluted with increasing concentrations of chloroform in petroleum ether. The eluate obtained with 20% v/v chloroform in petroleum ether on evaporation gave 2-[1-(dimethylcarbamoyl)ethylthio]-3-phenylquinoline as a viscous oil, which was used without further purification.

EXAMPLE 9

A solution of 2-dimethylaminoethanethiol hydrochloride (1.7 g.) in dimethylformamide (25 ml.) was added dropwise to a suspension of sodium hydride (0.5 g.) in a solution of 2-chloro-3-cyclopropylquinoline (2.0 g.) in dimethylformamide (25 ml.) at 0°–5°. The mixture was then heated at 80° for 4 hr. and then poured into ice water (200 ml.) and extracted with ethyl acetate (3×100 ml.). The ethyl acetate extract was washed successively with saturated brine (100 ml.) and water (3×100 ml.), dried (Na2SO4), and the solvent evaporated. The residue was chromatographed on silica gel (Merck 9385, 200 g.) using 10% v/v methanol in ethyl acetate as eluant. The appropriate fraction (monitored by thin layer chromatography) was evaporated, dissolved in methanol, and one equivalent of anhydrous oxalic acid was added. The solvent was evaporated and the residue crystallised from methanol/diethyl ether to give 3- cyclopropyl-2-(2-dimethylaminoethylthio)quinoline hydrogen oxalate, m.p. 158°.

The above procedure was repeated using the appropriate 2-chloroquinoline derivative as starting material to yield the compounds shown in the following table. Where indicated the hydrochloride salt was prepared using concentrated hydrochloric acid in place of oxalic acid.

[Structure: quinoline with R⁴, R⁵ substituents on benzene ring, R¹ at 3-position, SCH₂CH₂N(CH₃)₂ at 2-position]

| Example No. | R¹ | R⁴ | R⁵ | Salt | m.p. |
|---|---|---|---|---|---|
| 10 | n-propyl | H | H | hydrogen oxalate | 164-6 |
| 11 | o-methoxyphenyl | methyl | H | hydrogen oxalate | 164 |
| 12 | n-butyl | H | H | hydrochloride | 164-6 |
| 13 | s-butyl | H | H | hydrogen oxalate | 153-5 |
| 14 | 2-pyridyl | H | H | hydrogen oxalate | 134-6 |
| 15 | 2-thienyl | H | H | hydrogen oxalate | 184-94 |
| 16 | 3-thienyl | H | H | hydrogen oxalate | 167-9 |
| 17 | 2-methyl-4-thiazolyl | H | H | hydrogen oxalate | 167 |
| 18 | phenyl | H | methoxy | dihydrochloride | 84-5 |
| 19 | phenyl | methoxy | H | hydrogen oxalate | 176-8 |
| 20 | phenyl | H | n-propoxy | hydrogen oxalate | 174-5 |
| 21 | phenyl | H | methyl | hydrogen oxalate | 210-2 |
| 22 | phenyl | H | Br | hydrogen oxalate | 216-8 |
| 23 | phenyl | Cl | H | hydrogen oxalate | 200-2 |
| 24 | phenyl | Br | H | hydrogen oxalate | 208-10 |

Many of the 2-chloroquinoline derivatives used as starting material are novel compounds. They were prepared from the corresponding anilides by the method described in Example 1 to give the following compounds:

[Structure: quinoline with R⁴, R⁵ on benzene ring, R¹ at 3-position, Cl at 2-position]

| R¹ | R⁴ | R⁵ | m.p. |
|---|---|---|---|
| n-propyl | H | H | 31 |
| cyclopropyl | H | H | oil |
| s-butyl | H | H | oil |
| 2-pyridyl | H | H | 79-82 |
| 2-thienyl | H | H | oil |
| 3-thienyl | H | H | oil |
| 2-methyl-4-thiazolyl | H | H | 117-9 |
| phenyl | H | methoxy | 126-8 |
| phenyl | methoxy | H | oil |
| phenyl | H | n-propoxy | 65-7 |
| phenyl | H | methyl | 68-70 |

The following novel anilides were prepared as described in Example 1:

[Structure: aniline with R⁴, R⁵ substituents, NHCOCH₂R]

| R | R⁴ | R⁵ | mp/bp |
|---|---|---|---|
| o-methoxyphenyl | methyl | H | 86 |
| 3-thienyl | H | H | 123-5 |
| phenyl | H | Pr$^n$O | b.p. 95-8/0.5 mm |

Preparation of α-(2-methyl-4-thiazolyl)acetanilide

A solution of α-(2-methyl-4-thiazolyl)acetic acid (6.4 g.) and aniline (3.6 ml.) in dry methylene dichloride (50 ml.) was stirred at ambient temperature and dicyclohexylcarbodiimide (9 gm) was added in 1 g. portions over 30 min. The mixture was stirred at ambient temperature for 2 hr., filtered and the solvent evaporated. The solid residue was crystallised from aqueous ethanol to give the anilide, m.p. 124°.

Preparation of 6- and 7-halogeno-2-chloro-3-phenylquinolines

The method described in this Example for the preparation of 2-chloroquinoline derivatives is not suitable when the anilino moiety is substituted with a halogeno substituent. In these cases the following method was used:

6-Chloro-3-phenylquinolin-2-one (6.7 gm.) and phosphorus oxychloride (100 ml.) were heated together under reflux for 2 hr. The reaction mixture was then poured into ice water (1000 ml.) and extracted with ethyl acetate (3×100 ml.). The ethyl acetate extract was washed with water (3×50 ml.) and dried (Na₂SO₄), and the solvent was evaporated. The resulting solid was crystallised from ethanol to give 2,6-dichloro-3-phenylquinoline, m.p. 147°-9°.

Similarly prepared were 6-bromo-2-chloro-3-phenylquinoline, m.p. 136°-7°, and 7-bromo-2-chloro-3-phenylquinoline (as a mixture with the 5-bromo-isomer). The substituted quinolones used as starting material were prepared by the method of Manimaran and Ramahrishnan described in the Indian Journal of Chemisty, 1979, 18B, 324-330, and were used without purification.

EXAMPLES 25-38

The process described in Example 2 was repeated using an equivalent amount of the appropriate 2-chloro-3-(substituted phenyl)quinoline as starting material and there were thus obtained the following compounds:

[Structure: 3-phenylquinoline with R substituent on phenyl, SCH₂CH₂N(CH₃)₂·HCl at 2-position]

| Example No. | R | m.p. |
|---|---|---|
| 25 | m-methoxy | 191-3 |
| 26 | p-methoxy | 194-5 |
| 27 | p-chloro | 209-11 |
| 28 | p-bromo | 216-8 |

-continued

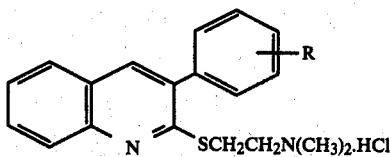

| Example No. | R | m.p. |
|---|---|---|
| 29 | p-n-propoxy | 156–62 |
| 30 | p-cyano | 251–2 |
| 31 | p-trifluoromethyl | 220–2 |
| 32 | 2,5-dimethoxy | 205 |
| 33 | p-methylthio | 208–11 |
| 34 | o-methyl | 207–9 |
| 35 | o-fluoro | 187–9 |
| 36 | o-chloro | 210–2 |
| 37 | m-fluoro | 169–71 |
| 38 | m-methyl | 157–9 |

The 2-chloroquinoline derivatives used as starting materials in Examples 25–38 were obtained from the appropriate anilide in an analogous manner to that described in Example 1:

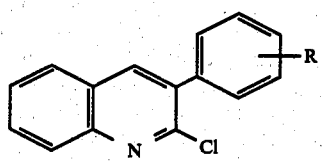

| R | m.p. |
|---|---|
| m-methoxy | oil |
| p-methoxy | 87–8 |
| p-chloro | 90–2 |
| p-bromo | 96–8 |
| p-n-propoxy | oil |
| p-cyano | 112–4 |
| p-trifluoromethyl | 89–92 |
| 2,5-dimethoxy | 102–4 |
| p-methylthio | 105–8 |
| o-methyl | 93–5 |
| o-fluoro | 111–3 |
| o-chloro | 116–8 |
| m-fluoro | 50–2 |
| m-methyl | 77–8 |

The following novel anilides, used as starting materials for the preparation of the corresponding 2-chloroquinolines, were prepared from aniline and the corresponding substituted phenylacetic acid in a manner analogous to that described in Example 2:

| R | m.p. |
|---|---|
| m-methoxy | 107–9 |
| p-methoxy | 115–6 |
| p-n-propoxy | 115 |
| p-trifluoromethyl | 154–6 |
| 2,5-dimethoxy | 118 |
| p-methylthio | 115–7 |
| o-fluoro | 127–9 |
| m-fluoro | 104–7 |
| m-methyl | 77–8 |

EXAMPLES 39 AND 40

The process described in Example 2 was repeated using an equivalent amount of 2-aminoethanethiol hydrochloride in place of 2-dimethylaminoethanethiol hydrochloride. There were thus obtained:
  2-(2-aminoethylthio)-3-phenylquinoline hydrochloride, m.p. 232°–7° (Example 39), and
  2-(2-aminoethylthio)-3-(o-methoxyphenyl)quinoline hydrochloride, m.p. 180° (Example 40).

EXAMPLES 41 AND 42

The process described in Example 6 was repeated using an equivalent amount of 3-n-butylquinolin-2-thione or 3-(o-methoxyphenyl)quinolin-2-thione as starting material in place of 3-phenylquinolin-2-thione. There were thus obtained:
  3-n-butyl-2-(2-methylaminoethylthio)quinoline hydrogen oxalate, m.p. 167°–9° (Example 41), and
  3-(o-methoxyphenyl)-2-(2-methylaminoethylthio)quinoline hydrochloride, m.p. 210° (Example 42), respectively.

EXAMPLE 43

The process described in Example 2 was repeated using an equivalent amount of 2-diethylaminoethanethiol hydrochloride in place of 2-dimethylaminoethanethiol hydrochloride. There was thus obtained 2-(2-diethylaminoethylthio)-3-phenylquinoline hydrochloride, m.p. 144°–6°.

EXAMPLE 44

Borane-dimethyl sulphide complex (0.37 ml.) was added dropwise to a solution of 2-(2-N-acetyl-N-methylaminoethylthio)-3-phenylquinoline (0.5 g.) in anhydrous tetrahydrofuran (10 ml.) under an atmosphere of argon. The mixture was heated under reflux for 4 hr. and then cooled. Methanol (2 ml.) was added and the mixture was allowed to stand at ambient temperature for 16 hr. The solvent was then evaporated, to the residue were added 2 M-hydrochloric acid (10 ml.) and methanol (5 ml.), and the mixture was heated on a steam bath for 1.5 hr. The solution was cooled to ambient temperature, basified with solid sodium bicarbonate, and extracted with ethyl acetate (3×15 ml.). The organic extract was washed with water (3×10 ml.), dried (Na₂SO₄), and evaporated to dryness under reduced pressure. The residue was chromatographed on silica gel (Merck 9385; 80 g.) using 10% v/v methanol in ethyl acetate as eluant. The desired fraction was collected and evaporated. The residue was dissolved in methanol and anhydrous oxalic acid (0.064 g.) was added. The resulting mixture was filtered and the solid residue was crystallised from methanol/ether to give 2-(2-N-ethyl-N-methylaminoethylthio)—3-phenylquinoline hydrogen oxalate hemihydrate, m.p. 179°–81°.

The 2-(2-N-acetyl-N-methylaminoethylthio)-3-phenylquinoline used as starting material was obtained as follows:

Acetyl chloride (0.2 ml.) was added to a solution of 2-(2-methylaminoethylthio)-3-phenylquinoline (0.8 g.) in methylene dichloride (25 ml.) and triethylamine (0.56 ml.), and the mixture was kept at ambient temperature for 1 hr. The mixture was washed successively with 2 M-hydrochloric acid (3×10 ml.) and water (3×10 ml.), dried (Na₂SO₄), and evaporated to dryness to give the N-acetyl derivative, which was used without further purification.

EXAMPLE 45

A 1 M-solution of tetra-n-butylammonium fluoride in tetrahydrofuran (12 ml.) was added to a solution of 2-{trans-2-[2-(trimethylsilyl)ethoxycarbonylamino]-cyclopropylthio}-3-phenylquinoline (3.5 g.) in dry acetonitrile (35 ml.), and the mixture was stirred at 50° under argon for 5 hr. The mixture was cooled, the solvent was evaporated, and the residual oil was partitioned between ethyl acetate (70 ml.) and water (35 ml.). The mixture was separated and the organic phase was washed with water (2×30 ml.) and dried ($Na_2SO_4$). The solvent was evaporated and the residual brown oil (2.7 g.) was chromatographed on basic alumina (180 gm., Brockmann, Grade III) eluted with 30% v/v chloroform in petroleum ether to give 2-(trans-2-aminocyclopropylthio)-3-phenylquinoline as a pale yellow oil, which gave a hydrochloride of m.p. 140°.

The quinoline derivative used as starting material was obtained as follows:

3-Phenylquinolin-2-thione (6.40 g.) was added portionwise to a stirred suspension of sodium hydride (1.34 g. of 50% w/w dispersion in mineral oil) in dry dimethylformamide (43 ml.) at 0° to 5° under argon. The mixture was stirred for 1 hr. at ambient temperature, and then a solution of cis/trans mixture of ethyl 2-bromocyclopropanecarboxylate (5.17 g.) in dimethylformamide (10 ml.) was added. The mixture was stirred for 2½ hr. at 90°, cooled to 10°, and poured into a mixture of water (700 ml.) and saturated brine (250 ml.). The mixture was extracted with ethyl acetate (5×120 ml.). The organic extract was washed with saturated brine (200 ml.), dried ($Na_2SO_4$), and the solvent evaporated. The residual yellow oil was chromatographed on basic alumina (210 g. Brockmann Grade III), eluted with petroleum ether to give 2-(trans-2-ethoxycarbonylcyclopropylthio)-3-phenylquinoline, m.p. 94°-4.5° (crystallised from isopropanol).

A solution of sodium hydroxide (0.37 g.) in water (3.6 ml.) was added to a solution of the above-mentioned ethoxycarbonyl derivative (2.43 g.) in t-butanol (90 ml.). The mixture was stirred for 16 hr. at 20° and then for 5 hr. at 40°. The mixture was cooled to ambient temperature, poured into a mixture of water (400 ml.) and saturated brine (200 ml.), and washed with diethyl ether (100 ml.). The aqueous phase was cooled to 5°, acidified to pH 3 with dilute hydrochloric acid, and extracted with ethyl acetate (5×150 ml.). The organic extract was dried ($Na_2SO_4$) and the solvent evaporated. The residual solid was crystallised from ethyl acetate/petroleum ether to give 2-(trans-2-carboxycyclopropylthio)-3-phenylquinoline, m.p. 168.5°-9.5°.

A solution of 2-(trans-2-carboxycyclopropylthio)-3-phenylquinoline (3.26 g.), diphenylphosphoryl azide (2.21 ml.) and triethylamine (1.43 ml.) in dry toluene (65 ml.) was stirred under argon for 2 hr. at 90°. 2-(Trimethylsilyl)ethanol (1.53 ml.) was added, and the reaction mixture was stirred for a further 16 hr. at 90°. The mixture was cooled to ambient temperature, washed with water (2×20 ml.), dried ($Na_2SO_4$), and the toluene removed under reduced pressure. The residual brown oil (5.5 g.) was purified on a basic alumina column (200 gm. Brockmann Grade III) by elution with 20% v/v chloroform in petroleum ether to give 2-{trans-2-[2-(trimethylsilyl)ethoxycarbonylamino]cyclopropylthio}-3-phenylquinoline as a light yellow oil, which was characterised by mass spectrometry, molecular ion equals 436, and by NMR ($CDCl_3$ solution, 90 MHz) multiplet 2.5 δ (2H, cyclopropane methine).

EXAMPLE 46

Sodium bis-(2-methoxyethoxy) aluminium hydride (a 3.4 M-solution in toluene, 3.2 ml.) was added to a solution of 2-(2-N-ethoxycarbonyl-N-methylaminoethylthio)-3-phenylquinoline (1.0 g.) in di-(2-methoxyethyl)ether (3.2 ml.) at 20° and under an atmosphere of argon. The mixture was heated at 85° for 2 hr. The mixture was cooled to ambient temperature, and the solvent was then evaporated under high vacuum (approx 0.5 mm.Hg.) at 20°. Water (10 ml.) and 2 M-sodium hydroxide (10 ml.) were added to the residue. The mixture was extracted with methylene dichloride (3×20 ml.). The organic extract was dried ($Na_2SO_4$), the solvent was evaporated, and the residue was chromatographed on silica gel (Merck 9385, 80 g.) using 5% v/v methanol in ethyl acetate, to give 2-(2-dimethylaminoethylthio)-3-phenylquinolene, identical to the product described in Example 2.

The ethoxycarbonyl derivative used as starting material was obtained as follows:

Ethyl chloroformate (0.5 ml.) was added to a solution of 2-(2-methylaminoethylthio)-3-phenylquinoline in methylene dichloride (20 ml.) and triethylamine (1.15 ml.), and the mixture was kept at ambient temperature for 1 hr. The mixture was then washed successively with 2 M-hydrochloride acid (3×100 ml.) and water (3×10 ml.), dried ($Na_2SO_4$), and the solvent evaporated. The residue was crystallised from ethanol to give 2-(2-N-ethoxycarbonyl-N-methylaminoethylthio)-3-phenylquinoline, m.p. 99°-101°.

EXAMPLE 47

2-Dimethylaminoethanethiol hydrochloride (0.88 g.) was added to a suspension of sodium hydride (1.1 g. of a 50% w/w dispersion in mineral oil) in dimethylformamide (50 ml.) at 0°-5°. When all the hydrogen had evolved, a solution of 2-chloro-3-p-hydroxyphenylquinoline (1.6 g.) in dimethylformamide (10 ml.) was added and the mixture was stirred at ambient temperature for 16 hr. Additional 2-dimethylaminoethanethiol hydrochloride (0.32 g.), followed by a suspension of sodium hydride (0.4 g. of a 50% w/w dispersion in mineral oil), was added and the mixture was heated at 65° for 2 hr. The mixture was then cooled to ambient temperature, poured into water (500 ml.), and adjusted to pH 2 with 2 M-hydrochloric acid. The solution was then adjusted to pH 8 with saturated sodium bicarbonate solution and extracted with ethyl acetate (2×100 ml.). The ethyl acetate extract was washed with water (2×50 ml.) and dried ($MgSO_4$). The solvent was evaporated, the residue was dissolved in diethyl ether (200 ml.), and ethereal hydrogen chloride was added. The solvent was evaporated, and the residue was crystallised from ethanol-diethyl ether to give 2-(2-dimethylaminoethylthio)-3-(p-hydroxyphenyl)quinoline hydrochloride, m.p. 220°-2°.

The quinoline derivative used as starting material was obtained as follows:

A mixture of p-acetoxyphenylacetic acid (6.2 g.), oxalyl chloride (10 g.) and dimethylformamide (2 drops) was stirred at ambient temperature for 16 hr. The excess oxalyl chloride was evaporated, the residue was dissolved in methylene dichloride (50 ml.), and the solution was added dropwise to a stirred ice-cold solution of aniline (3 g.) and triethylamine (3.2 g.) in methylene dichloride (50 ml.). The mixture was stirred at ambient temperature for 3 hr. and then washed successively with 2 M-hydrochloric acid (25 ml.), water (25 ml.), saturated sodium carbonate solution (10 ml.), water (2×25 ml.), and then dried (MgSO$_4$). The solvent was evaporated and the residue, consisting of p-acetoxyphenylacetanilide, was used without further purification.

Dimethylformamide (1.7 g.) was added dropwise with stirring to phosphorus oxychloride (10 ml.) at 0°–5°, and p-acetoxyphenylactanilide (4 g.) was then added. The mixture was heated at 75° for 16 hr., cooled to ambient temperature, poured into water (600 ml.) and extracted with ethyl acetate (3×100 ml.). The ethyl acetate extract was washed successively with saturated sodium carbonate solution (25 ml.) and water (2×25 ml.), and then dried (MgSO$_4$). The solvent was evaporated and the residual oil was chromatographed on basic alumina (200 g., Brockmann Grade III), eluted with increasing concentrations of chloroform in petroleum ether, followed by methanol in chloroform. The eluate obtained with 1% v/v methanol in chloroform was evaporated. The residue was crystallised from ethyl acetate-petroleum ether to give 2-chloro-3-(p-hydroxyphenyl)quinoline, m.p. 164°–6°.

EXAMPLE 48

Sodium hydride (0.68 g. of a 50% w/w dispersion in mineral oil) was added to a solution of 3-phenylquinolin-2-thione (1.6 g.) in dimethylformamide (10 ml.) at ambient temperature. When all the hydrogen had evolved, trans-2-chlorocyclohexylamine hydrochloride (1.2 g.) was added and the reaction mixture was stirred at 60° for 20 hr. The reaction mixture was cooled to ambient temperature, diluted with water (100 ml.), and extracted with ethyl acetate (2×30 ml.). The ethyl acetate extract was washed with water (2×10 ml.) and then dried (MgSO$_4$). The solvent was evaporated and the residue was chromatographed on basic alumina (100 g., Brockmann Grade III), eluted with increasing concentrations of chloroform in petroleum ether, followed by chloroform. The chloroform eluate was evaporated. The residue was dissolved in diethyl ether (100 ml.), and ethereal hydrogen chloride was added until precipitation was complete. The solvent was evaporated and the residue was crystallised from ethyl acetate to give 2-(trans-2-aminocyclohexylthio)-3-phenylquinoline hydrochloride, m.p. 223°–5°.

EXAMPLE 49

Formaldehyde (3.2 ml. of a 37% w/v solution in water) was added to a solution of 2-(trans-2-aminocyclohexylthio)-3-phenylquinoline (1.7 g.) in formic acid (4 ml.) at ambient temperature. The mixture was heated under reflux for 16 hr. The mixture was cooled to ambient temperature and poured into water (50 ml.). The mixture was adjusted to pH 10 with 2 N-sodium hydroxide solution, and extracted with ethyl acetate (3×15 ml.). The ethyl acetate extract was washed with water (3×10 ml.) and dried (MgSO$_4$). The solvent was evaporated and the residue was chromatographed on basic alumina (100 g. Brockmann Grade III), eluted with increasing concentrations of chloroform in petroleum ether. The eluate obtained with 20% v/v chloroform in petroleum ether was evaporated. The residue was dissolved in diethyl ether (25 ml.), and ethereal hydrogen chloride was added until precipitation was complete. The solvent was evaporated and the residue was crystallised from ethyl acetate to give 2-(trans-2-dimethylaminocyclohexylthio)-3-phenylquinoline hydrochloride, m.p. 199°–202°.

The 2-(trans-2-aminocyclohexylthio)-3-phenylquinoline used as starting material was obtained by following the procedure described in Example 48 up to the stage where the chloroform eluate was evaporated.

EXAMPLE 50

Sodium hydride (0.48 g. of a 50% w/w dispersion in mineral oil) was washed with petroleum ether (25 ml.) under an atmosphere of argon. The solvent was decanted, dimethylsulphoxide (5 ml.) was added, and the mixture was heated at 50° for 1 hr. The mixture was cooled to ambient temperature and water (0.18 ml.) was added, followed by a solution of methyl N-[cis-2-(3-phenyl-2-quinolylthio)cyclohexyl]carbamate (1.3 g.) in dimethylsulphoxide (5 ml.). The mixture was stirred at ambient temperature for 1 hr. and then at 50° for 1.5 hr. The mixture was cooled to ambient temperature, diluted with water (100 ml.), and extracted with ethyl acetate (2×25 ml.). The ethyl acetate extract was washed with water (2×10 ml.) and dried (MgSO$_4$). The solvent was evaporated and the residue was chromatographed on basic alumina (100 g. of Brockmann Grade III), eluted with increasing concentrations of chloroform in petroleum ether. The eluate obtained with 60% v/v chloroform in petroleum ether was evaporated, the residue was dissolved in diethyl ether (50 ml.), and ethereal hydrogen chloride was added to the solution until precipitation was complete. The solvent was evaporated and the residue was crystallised from ethyl acetate to give 2-(cis-2-aminocyclohexylthio)-3-phenylquinoline hydrochloride, m.p. 170°–5° (dec.).

The carbamate used as starting material was obtained as follows:

Sodium hydride (0.24 g. of a 50% w/w dispersion in mineral oil) was added to a solution of 3-phenylquinolin-2-thione (1.19 g.) in dimethylformamide (10 ml.) at ambient temperature. When all the hydrogen had evolved, methyl N-(trans-2-iodocyclohexyl)carbamate (1.4 g.) was added and the mixture was stirred at 60° for 4 hr. The mixture was cooled to ambient temperature, diluted with water (100 ml.), and extracted with ethyl acetate (2×25 ml.). The organic extract was washed with water (2×10 ml.) and dried (MgSO$_4$). The solvent was evaporated and the gummy residue, containing methyl N-[cis-2-(3-phenyl-2-quinolylthio)cyclohexyl]carbamate, was used without further purification.

EXAMPLE 51

A mixture of 3-(p-cyanophenyl)-2-(2-dimethylaminoethylthio)quinoline hydrochloride (see Ex. 30, 0.65 g.), t-butanol (25 ml.) and potassium hydroxide (0.6 g.) was heated at 40° for 1 hr. Water (20 ml.) was added to the mixture and the t-butanol was evaporated. Additional water (20 ml.) was added, and the mixture was extracted with chloroform (3×30 ml.). The chloroform extract was washed with water (2×10 ml.) and dried (MgSO$_4$). The solvent was evaporated and the residue was crystallised from ethanol. The crystalline material was dissolved in ethanol (50 ml.) and ethereal hydrogen chloride was added to the solution. The solvents were evaporated and the residue was crystallised from ethanol-diethyl ether to give 3-(p-carbamoylphenyl)-2-(2-dimethylaminoethylthio)quinoline hydrochloride, m.p. 253°–5°.

EXAMPLE 52

3-(p-Carboxyphenyl)quinolin-2-thione (6.87 g.) was added to a suspension of sodium hydride (3.9 g. of a 50% w/w dispersion in mineral oil) in dimethylformamide (50 ml.) at 0°–5°. When all the hydrogen had evolved, 2-dimethylaminoethyl chloride hydrochloride (3.5 g.) was added and the mixture was stirred at ambient temperature for 16 hr. The mixture was poured into ice-water (300 ml.), filtered, and the filtrate adjusted to pH 7 with 2 M-hydrochloric acid. The resulting mixture was filtered and the solid residue was dissolved in 2 M-hydrogen chloride in methanol at 0°. The solvent was evaporated and the solid residue was crystallised from methanol-ethyl acetate to give 3-(p-carboxyphenyl)-2-(2-dimethylaminoethylthio)quinoline hydrochloride, m.p. 246°–7°.

The quinoline derivative used as starting material was obtained as follows:

3-(p-Cyanophenyl)quinolin-2-thione (0.26 g.) was added to hydrogen bromide (2 ml. of a 48% w/v aqueous solution) and the mixture was heated at 140° for 3 hr. The mixture was cooled to ambient temperature and poured into ice-water (20 ml.). The resulting mixture was filtered, the solid residue was stirred with hot ethanol (20 ml.) for 5 min. and then filtered. There was thus obtained as the solid residue 3-(p-carboxyphenyl)quinolin-2-thione, m.p. >300°.

The cyano derivative used as starting material was obtained as follows:

A mixture of 2-chloro-3-(p-cyanophenyl)quinoline (6.25 g., see Example 30) and thiourea (1.8 g.) in ethanol (30 ml.) was heated under reflux for 2 hr. The solution was allowed to cool to ambient temperature, the solid which precipitated was filtered off, dispersed in 1 M-sodium hydroxide solution (100 ml.) and the dispersion heated on a steam bath for 20 min. The mixture was acidified with 2 M-hydrochloric acid solution. The resulting mixture was filtered, the solid residue was stirred with hot ethanol (75 ml.) for 5 min., and the mixture was then filtered. There was thus obtained as the solid residue 3-(p-cyanophenyl)quinolin-2-thione, m.p. 284°–9°.

EXAMPLE 53

Oxalyl chloride (2.35 ml.) and dimethylformamide (1 drop) were added to a solution of 3-(p-carboxyphenyl)-2-(2-dimethylaminoethylthio)quinoline (0.7 g.) in methylene dichloride (30 ml.), and the mixture was stirred at ambient temperature for 16 hr. The solvent was evaporated, the residue was dissolved in dimethylformamide (5 ml.) and the solution was heated at 150° for 4 hr. The mixture was poured into ice-water (50 ml.), and the solution was adjusted to pH 10 with saturated potassium carbonate solution and extracted with ethyl acetate (3×20 ml.). The ethyl acetate extract was washed with saturated brine (20 ml.), dried (MgSO$_4$) and the solvent evaporated. The residue was dissolved in diethyl ether (10 ml.) and ethereal hydrogen chloride was added until precipitation was complete. The mixture was filtered and the solid residue was crystallised from methanol-ethyl acetate to give 2-(2-dimethylaminoethylthio)-3-(p-dimethylcarbamoylphenyl)quinoline hydrochloride, m.p. 199°–201°.

EXAMPLE 54

3-(p-Carboxyphenyl)-2-(2-dimethylaminoethylthio)quinoline (0.7 g.) was added to a solution of thionyl chloride (1.5 ml.) in methanol (20 ml.) at 0°. The mixture was stirred at ambient temperature for 16 hr., and the solvent then evaporated. The solid residue was crystallised from methanol-ethyl acetate to give 2-(2-dimethylaminoethylthio)-3-(p-methoxycarbonylphenyl)quinoline hydrochloride, m.p. 224-5°.

EXAMPLE 55

Sodium hydride (0.96 g. of a 50% w/w dispersion in mineral oil) was added to a solution of 3-phenylquinolin-2-thione (2.37 g.) in dimethylformamide (100 ml.) at ambient temperature. When all the hydrogen had evolved, 2-chloromethyl-1-methylpiperidine hydrochloride (1.84 g.) was added and the mixture was stirred at ambient temperature for 16 hr. The mixture was then poured into water (750 ml.) and extracted with ethyl acetate (2×150 ml.). The ethyl acetate extract was washed with water (2×50 ml.) and then dried (MgSO$_4$). The solvent was evaporated and the residue was chromatographed on basic alumina (150 g. Brockmann Grade III), eluted with increasing concentrations of chloroform in petroleum ether. The eluate obtained with 20% v/v chloroform in petroleum ether was evaporated. The residue was dissolved in diethyl ether (50 ml.) and ethereal hydrogen chloride was added until precipitation was complete. The solid was collected by filtration and crystallised from ethanol-diethyl ether to give 2-[(1-methyl-2-piperidylmethylthio]-3-phenylquinoline hydrochloride, m.p. 198°–200°.

EXAMPLE 56

A solution of 3-(p-fluorophenyl)-2-(2-oxopropylthio)quinoline (2.94 g.) in dry ethanol (120 ml.) was added to a mixture of dimethylamine in ethanol (8.5 ml. of a 33% w/v solution) and glacial acetic acid (1.1 ml.). Sodium cyanoborohydride (0.42 g.) was then added. The mixture was stirred for 96 hr. at ambient temperature in the presence of a molecular sieve (2.0 g. of type 3A). The molecular sieve was filtered off and the solvent evaporated. 2 M-hydrochloric acid solution (25 ml.) was added to the residue and the mixture was washed with ethyl acetate (20 ml.). The aqueous phase was basified with 2 M-sodium hydroxide solution (30 ml.), and the mixture was extracted with diethyl ether (3×50 ml.). The ethereal extract was washed with brine (50 ml.) and dried (MgSO$_4$). The solvent was evaporated and the residue chromatographed on basic alumina (100 g., Brockmann Grade III), eluted with increasing concentrations of ethyl acetate in petroleum ether. The eluate obtained with 10% v/v ethyl acetate in petroleum ether was evaporated. The residue was dissolved in diethyl ether (25 ml.) and ethereal hydrogen chloride was added until precipitation was complete. The solid was collected by filtration and crystallised from ethyl acetate to give 2-(2-dimethylaminopropylthio)-3-(p-fluorophenyl)quinoline hydrochloride, m.p. 176°–8°.

The quinoline derivative used as starting material was obtained as follows:

3-(p-Fluorophenyl)quinolin-2-thione (5.05 g.) was added in portions to a stirred suspension of sodium hydride (1.0 g. of a 50% w/w dispersion in mineral oil) in dimethylformamide (30 ml.) at 0°–5°. When all the hydrogen had evolved, chloroacetone (1.83 g.) was added and the mixture was stirred at ambient temperature for 18 hr. The mixture was poured into ice-water (300 ml.) and extracted with ethyl acetate (3×100 ml.). The ethyl acetate extract was washed with brine (75 ml.) and then dried (MgSO$_4$). The solvent was evaporated and the residue was chromatographed on basic alumina (200 g., Brockmann Grade III), eluted with increasing concentrations of ethyl acetate in petroleum ether. The eluate obtained with 10% v/v ethyl acetate in petroleum ether was evaporated to give 3-(p-fluorophenyl)-2-(2-oxopropylthio)quinoline, m.p. 95°–96°.

3-(p-Fluorophenyl)quinolin-2-thione itself was obtained as follows:

A mixture of 2-chloro-3-(p-fluorophenyl)quinoline (6.03 g., see Example 3) and thiourea (1.8 g.) in ethanol (30 ml.) was heated under reflux for 2 hr. The solution was allowed to cool to ambient temperature, the solid which precipitated was filtered off, dispersed in 1 M-sodium hydroxide solution (100 ml.), and the dispersion heated on a steam bath for 20 min. The mixture was acidified with 2 M-hydrochloric acid solution. The resulting mixture was filtered, the solid residue was stirred with hot ethanol (75 ml.) for 5 min., and then filtered. There was thus obtained as the solid residue 3-(p-fluorophenyl)quinolin-2-thione, m.p. 259°–262°.

EXAMPLE 57

(S)-2-(2-t-Butoxycarbonylaminopropylthio)-3-phenylquinoline (3.9 g.) was added to 6 M-hydrogen chloride in ethyl acetate (50 ml.) and the mixture was stirred at ambient temperature for 1 hr. The solvent was evaporated and the residual oil was dissolved in diethyl ether (100 ml.) and extracted with 1 M-hydrochloric acid (6×25 ml.). The hydrochloric acid extract was adjusted to pH 10 with saturated sodium carbonate solution and extracted with diethyl ether (2×50 ml.). The diethyl ether extract was dried (MgSO$_4$) and ethereal hydrogen chloride was added until precipitation was complete. The solid residue was collected by filtration and crystallised from methanol-ethyl acetate to give (+)-(S)-2-(2-aminopropylthio)-3-phenylquinoline hydrochloride, m.p. 223°–4°, $[\alpha]_D^{25}$ +39.7° (C, 0.78 in methanol).

The quinoline derivative used as starting material was obtained as follows:

Di-t-butyl carbonate (15.7 g.) was added to a solution of (+-(S)-2-amino-1-propanol (5.0 g.) in water (13.2 ml.) and t-butanol (6.6 ml.) at ambient temperature, and the mixture was stirred for 16 hr. at ambient temperature, 1,1-Dimethylethylenediamine (2 ml.) was added and the mixture was stirred at ambient temperature for 1 hr. The solution was poured into water (200 ml.) and extracted with diethyl ether (3×100 ml.). The ethereal extract was washed successively with 1 M-hydrochloric acid (50 ml.), saturated sodium carbonate solution (50 ml.) and brine (100 ml.), and then dried (MgSO$_4$). The solvent was evaporated to give (S)-2-t-butoxycarbonylamino-1-propanol, m.p. 42°–3°.

p-Toluenesulphonyl chloride (4.2 g.) was added to a solution of (S)-2-t-butoxycarbonylamino-1-propanol (3.5 g.) in pyridine (10 ml.) at 0°. The mixture was kept at 0°–5° for 20 hr. and then poured into ice-water (200 ml.) and extracted with diethyl ether (3×50 ml.). The diethyl ether extract was washed successively with 1 M-hydrochloric acid (50 ml.), saturated sodium carbonate solution (50 ml.) and brine (50 ml.), and then dried (MgSO$_4$). The solvent was evaporated and the residue was crystallised from ethyl acetate-petroleum ether to give (S)-2-t-butoxycarbonylamino-1-toluenesulphonyloxypropane, m.p. 73°–4°.

3-Phenylquinolin-2-thione (2.5 g.) was added to a suspension of sodium hydride (0.55 g. of a 50% w/w dispersion in mineral oil) in dimethylformamide (16 ml.) at 0°–5°. When all the hydrogen had evolved, (S)-2-t-butoxycarbonylamino-1-p-toluenesulphonyloxypropane (3.5 g.) was added and the mixture was stirred at ambient temperature for 16 hr. The mixture was then poured into ice-water (160 ml.) and extracted with ethyl acetate (3×50 ml.). The ethyl acetate extract was washed with brine (50 ml.) and then dried (MgSO$_4$). The solvent was evaporated and the residue was crystallised from petroleum ether to give (S)-2-(2-t-butoxycarbonylaminopropylthio)-3-phenylquinoline, m.p. 86°–7°.

EXAMPLE 58

Formaldehyde (3.2 ml. of a 37% w/v solution in water) was added to a solution of (+)-(S)-2-(2-aminopropylthio)-3-phenylquinoline (1.55 g.) in formic acid (4 ml.) at ambient temperature, and the mixture was heated under reflux for 16 hr. The mixture was evaporated and the residual oil was dissolved in water (10 ml.). The solution was adjusted to pH 10 with saturated sodium carbonate solution and extracted with diethyl ether (2×10 ml.). The diethyl ether extract was washed with brine (10 ml.) and dried (MgSO$_4$). The solvent was evaporated and the solid residue was chromatographed on basic alumina (80 g. Brockmann Grade III), eluted with increasing concentrations of methylene dichloride in petroleum ether. The eluate obtained with 10% v/v methylene dichloride in petroleum ether was evaporated. The residual solid was dissolved in diethyl ether (10 ml.) and ethereal hydrogen chloride was added until precipitation was complete. The mixture was filtered and the solid residue was crystallised from ethyl acetate to give (−)-(S)-2-(2-dimethylaminopropylthio)-3-phenylquinoline hydrochloride, m.p. 167°–8°, $[\alpha]_D^{25}$ −36.3° (C, 2.0 in methanol).

The (+)-S-(2-aminopropylthio)-3-phenylquinoline used as starting material was obtained from the corresponding hydrochloride (see Example 57) by dissolving the latter in water, basifying the solution with a dilute aqueous sodium hydroxide solution, extracting with ethyl acetate, washing the extract with water, drying the extract (Na$_2$SO$_4$), and evaporating the solvent, thus giving the required compound, which was used without further purification.

EXAMPLE 59

Formaldehyde (5.3 ml. of a 37% w/v solution in water) was added to a solution of 3-phenyl-2-(3-piperidylthio)quinoline (2.85 g.) in formic acid (6.7 ml.) at ambient temperature. The mixture was heated under reflux for 16 hr. The mixture was evaporated and the residual oil was dissolved in water (15 ml.). The solution was adjusted to pH 10 with 2 M-sodium hydroxide solution and extracted with diethyl ether (2×15 ml.). The diethyl ether extract was washed with brine (15 ml.) and then dried (MgSO$_4$). The solvent was evaporated and the residual oil chromatographed on basic alumina (120 g., Brockmann Grade III), eluted with increasing concentrations of ethyl acetate in petroleum ether. The eluate obtained with 10% v/v ethyl acetate in petroleum ether was evaporated, the residual solid dissolved in diethyl ether (15 ml.), and ethereal hydrogen chloride was added until precipitation was complete. The mixture was filtered and the solid residue was crystallised from ethyl acetate to give 2-(1-methyl-3-piperidylthio)—3-phenylquinoline hydrochloride, m.p. 221°–3°.

The quinoline derivative used as starting material was obtained as follows:

Di-t-butyl carbonate (11.9 g.) was added to a solution of 3-hydroxypiperidine (5.0 g.) in water (10 ml.) and t-butanol (5 ml.) at ambient temperature, and the mixture was stirred for 16 hr. at ambient temperature. 1,1-Dimethylethylenediamine (1.5 ml.) was added and the mixture was stirred at ambient temperature for 1 hr. The solution was poured into water (150 ml.) and extracted with diethyl ether (3×50 ml.). The diethyl ether extract was washed successively with 1 M-hydrochloric acid (50 ml.), saturated sodium carbonate solution (50 ml.) and brine (50 ml.), and then dried ($MgSO_4$). The solvent was evaporated to give 1-t-butoxycarbonyl-3-hydroxypiperidine, which was used without further purification.

p-Toluenesulphonyl chloride (5.8 g.) was added to a solution of the above-mentioned t-butoxycarbonyl derivative (6.0 g.) in pyridine (20 ml.) at 0°. The mixture was kept at 0°-5° for 20 hr., then poured into ice-water (400 ml.), and extracted with diethyl ether (3×100 ml.). The diethyl ether extract was washed successively with 1 M-hydrochloric acid (100 ml.), saturated sodium carbonate solution (100 ml.) and brine (100 ml.), and then dried ($MgSO_4$). The solvent was evaporated to give 1-t-butoxycarbonyl-3-p-toluenesulphonyloxypiperidine, which was used without further purification.

3-Phenylquinolin-2-thione (5.2 g.) was added to a suspension of sodium hydride (1.15 g. of a 50% w/w dispersion in mineral oil) in dimethylformamide (35 ml.) at 0°-5°. When all the hydrogen had evolved, 1-t-butoxycarbonyl-3-p-toluenesulphonyloxypiperidine (7.8 g.) was added and the mixture was heated at 80° for 2 hr. The mixture was cooled to ambient temperature poured into ice-water (350 ml.) and extracted with ethyl acetate (3×150 ml). The ethyl acetate extract was washed with brine (150 ml.) and then dried ($MgSO_4$). The solvent was evaporated to give 2-(1-t-butoxycarbonyl-3-piperidylthio)—3-phenylquinoline, which was used without further purification.

2-(1-Butoxycarbonyl-3-piperidylthio)—3-phenylquinoline (4.2 g.) was added to 6 M-hydrogen chloride in ethyl acetate (50 ml.), and the mixture was stirred at ambient temperature for 1 hr. The solvent was evaporated and the residual oil was dissolved in diethyl ether (100 ml.) and extracted with 1 M-hydrochloric acid solution (20×30 ml.). The hydrochloric acid extract was adjusted to pH 10 with saturated sodium carbonate solution and extracted with diethyl ether (2×100 ml.). The diethyl ether extract was washed with brine (75 ml.) and then dried ($MgSO_4$). The solvent was evaporated to give 3-phenyl-2-(3-piperidylthio)quinoline which was used without further purification.

EXAMPLE 60

3-Phenylquinolin-2-thione (1.4 g.) was added to a suspension of sodium hydride (0.68 g. of a 50% w/w dispersion in mineral oil) in dimethylformamide (10 ml.) at 0°-5°. When all the hydrogen had evolved, a slurry of 1-chloro-2-dimethylamino-2-methylpropane hydrochloride (1.1 g.) in dimethylformamide (10 ml.) was added and the mixture was stirred at ambient temperature for 20 hr. The mixture was then poured into ice-water (100 ml.) and extracted with ethyl acetate (3×30 ml.). The ethyl acetate extract was washed with brine (30 ml.) and then dried ($MgSO_4$). The solvent was evaporated and the residual oil was chromatographed on basic alumina (125 g., Brockmann Grade III), eluted with increasing concentrations of methylene dichloride in petroleum ether. The eluate obtained with 10% v/v methylene dichloride in petroleum ether was evaporated, the residual oil was dissolved in diethyl ether (20 ml.), and ethereal hydrogen chloride was added until precipitation was complete. The mixture was filtered and the solid residue was crystallised from ethyl acetate to give 2-(2-dimethylamino-2-methylpropylthio)-3-phenylquinoline hydrochloride, m.p. 199°-201°.

EXAMPLE 61

Borane-dimethyl sulphide (1.2 ml. of a 1 M-solution) was added to a solution of 2-(1-dimethylcarbamoyl-1-methylethylthio)-3-phenylquinoline (2.1 g.) in tetrahydrofuran (60 ml.) at ambient temperature and under an atmosphere of argon. The mixture was heated under reflux for 4 hr. Methanol (20 ml.) was added and the mixture was heated under reflux for 2 hr. The solvents were evaporated and the residual oil was chromatographed on basic alumina (150 g., Brockmann Grade III), eluted with increasing concentrations of ethyl acetate in petroleum ether. The eluate obtained with 2% v/v ethyl acetate in petroleum ether was evaporated. The residual oil was dissolved in diethyl ether (20 ml.) and ethereal hydrogen chloride was added until precipitation was complete. The mixture was filtered and the solid residue was crystallised from methanol-ethyl acetate to give 2-(1,1-dimethyl-2-dimethylaminoethylthio)-3-phenylquinoline hydrochloride, m.p. 223°-4°.

The quinoline derivative used as starting material was obtained as follows:

3-Phenylquinolin-2-thione (1.18 g.) was added to a suspension of sodium hydride (0.46 g. of a 50% w/w dispersion in mineral oil) in dimethylformamide (10 ml.) at 0°-5°. When all the hydrogen had evolved, 2-bromoisobutyric acid (0.88 g.) was added and the mixture was heated at 80° for 16 hr. The mixture was cooled to ambient temperature, poured into ice-water (50 ml.), acidified to pH 2 with concentrated hydrochloric acid, and extracted with ethyl acetate (3×25 ml.). The ethyl acetate extract was washed with brine (25 ml.) and then dried ($MgSO_4$). The solvent was evaporated and the residual oil was chromatographed on silica (100 g., Merck type 7734), eluted with increasing concentrations of ethyl acetate in petroleum ether. The eluate obtained with 10% v/v ethyl acetate in petroleum ether was evaporated and the solid residue crystallised from cyclohexane to give 2-(1-carboxy-1-methylethylthio)-3-phenylquinoline, m.p. 144°-6°.

Oxalyl chloride (3 ml.) and dimethylformamide (2 drops) were added to a solution of 2-(1-carboxy-1-methylethylthio)-3-phenylquinoline (5.64 g.) in methylene dichloride (35 ml.), and the mixture was stirred at ambient temperature for 16 hr. The solvent was evaporated, the solid residue was dissolved in toluene (250 ml.), and a solution of dimethylamine in toluene (30 ml. of a 6 M-solution) was added at 0°. The mixture was stirred at ambient temperature for 20 hr., poured into water (200 ml.), and the mixture separated, both phases being retained. The aqueous phase was extracted with ethyl acetate (2×50 ml.), and the combined ethyl acetate and toluene phases were washed with brine (100 ml.) and then dried ($MgSO_4$). The solvent was evaporated and the solid residue was chromatographed on basic alumina (150 g., Brockmann Grade III), eluted with increasing concentrations of ethyl acetate in petroleum ether. The eluate obtained with 5% v/v ethyl acetate in petroleum ether was evaporated to give 2-(1- dimethylcarbamoyl-1-methylethylthio)-3-phenylquinoline, m.p. 149°–156°.

EXAMPLE 62

Methyl iodide (0.85 g.) was added to a mixture of 2-(2-methylaminoethylthio)-3-phenylquinoline hydrochloride (1.65 g.) and potassium carbonate (1.65 g.) in dry ethanol (50 ml.) at ambient temperature. The mixture was stirred at ambient temperature for 3 hr. and the solvent was then evaporated. The residue was dissolved in water (50 ml.) and extracted with diethyl ether (3×25 ml.). The diethyl ether extract was washed with brine (25 ml.), dried (MgSO₄), and the solvent evaporated. The residual oil was chromatographed on basic alumina (75 g., Brockmann Grade III), eluted with increasing concentrations of methylene dichloride in petroleum ether. The eluate with 50% v/v methylene dichloride in petroleum ether was evaporated. The residue was dissolved in diethyl ether (25 ml.) and ethereal hydrogen chloride added until precipitation was complete. The mixture was filtered and the solid residue was crystallised from methanol-ethyl acetate to give 2-(2-dimethylaminoethylthio)-3-phenylquinoline hydrochloride, m.p. 196°–8°.

What we claim is:

1. A quinoline derivative of the formula:

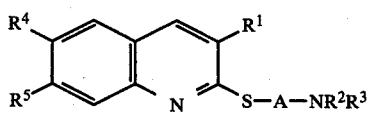

wherein:

A is a member selected from the group consisting of the radical —(CH$_2$)$_2$—, the radical —(CH$_2$)$_2$— which is substituted by not more than two (1-2C)alkyl radicals, and the radical —(CH$_2$)$_2$— which is substituted by an alkylene radical so as to form, together with the residue of the —(CH$_2$)$_2$— radical, a cycloalkylene radical of not more than 6 carbon atoms;

R$^1$ is a member selected from the group consisting of n-, iso- and s-(3-4C)alkyl, cyclopropyl and phenyl; and phenyl which bears not more than two substituents selected from the group consisting of halogen, hydroxy, (1-4C)alkyl, (1-4C)alkoxy, (1-4C)alkylthio, (1-2C)perfluoroalkyl, cyano, carboxy, (1-2C)alkoxy-carbonyl, carbamoyl, N-[(1-3C)alkyl]-carbamoyl and N,N-di-[(1-3C)alkyl]carbamoyl; and furyl, thienyl, pyridyl, thiazolyl or oxazolyl, any of which may optionally be substituted by (1-2C)alkyl;

R$^2$ is a member selected from the group consisting of hydrogen, methyl and ethyl, and dimethylene, trimethylene or tetramethylene which is linked to one or other of the carbon atoms forming the two-carbon-atom-backbone of radical A so as to form, together with the adjacent nitrogen atom, a pyrrolidinyl or piperidyl radical;

R$^3$ is a member selected from the group consisting of hydrogen, methyl and ethyl; and one or R$^4$ and R$^5$ stands for hydrogen, and the other is a member selected from the group consisting of hydrogen, halogen atoms, (1-3C)alkyl and (1-3C)alkoxy;

or a pharmaceutically-acceptable acid-addition salt thereof.

2. A compound as claimed in claim 1 wherein A is a member selected from the group consisting of 1,2-ethylene, 1,2-propylene, 2,3-propylene, 1,1-dimethyl-1,2-ethylene, 2,2-dimethyl-1,2-ethylene, cyclopropylene, 1,2-cis-cyclohexylene and 1,2-trans-cyclohexylene.

3. A compound as claimed in claim 1 wherein R$^1$ is a member selected from the group consisting of n-propyl, isopropyl, n-butyl, s-butyl, cyclopropyl and phenyl; and phenyl which is substituted by not more than two substituents selected from fluorine, chlorine and bromine atoms and hydroxy, (1-2C)alkyl, (1-4C)-alkoxy, (1-2C)alkylthio, trifluoromethyl, cyano carboxy, (1-2C)alkoxy-carbonyl, carbamoyl, N-[(1-2C)alkyl]carbamoyl and N,N-di-[(1-2C)alkyl]carbamoyl; and furyl, thienyl, pyridyl, thiazolyl, oxazolyl, (1-2C)alkyl-furyl, (1-2C)alkyl-thienyl, (1-2C)alkyl-pyridyl, (1-2C)alkyl-thiazolyl and (1-2C)alkyl-oxazolyl.

4. A compound as claimed in claim 1 which is a member selected from the group consisting of 2-(2-dimethylaminoethylthio)-3-isopropylquinoline, 2-(2-dimethylaminoethylthio)-3-p-fluorophenylquinoline, 2-(2-dimethylaminoethylthio)-3-o-methoxyphenylquinoline, 2-(2-dimethylaminoethylthio)-3-p-tolylquinoline, 2-(2-dimethylamino-2-methylpropylthio)-3-phenylquinoline and 2-(2-dimethylaminopropylthio)-3-phenylquinoline, and pharmaceutically-acceptable acid-addition salts thereof.

5. A compound as claimed in claim 1 which is a member selected from the group consisting of 2-(2-dimethylaminoethylthio)-3-phenylquinoline and pharmaceutically-acceptable acid-addition salts thereof.

6. A pharmaceutical composition for use as a 5-hydroxytryptamine antagonist comprising an effective amount of a quinoline derivative of the formula I, wherein A, R$^1$, R$^2$, R$^3$, R$^4$ and R$^5$ have the meanings stated in claim 1, or a pharmaceutically-acceptable acid-addition salt thereof, and an inert pharmaceutically-acceptable diluent or carrier.

7. The method of inhibiting the activity of 5-hydroxytryptamine in warm-blooded animals which comprises administering to such animals an effective amount of a compound according to claim 1.

* * * * *